United States Patent
Jones et al.

(10) Patent No.: US 8,014,873 B2
(45) Date of Patent: Sep. 6, 2011

(54) APPARATUS FOR IMPLANTING AN ELECTRICAL STIMULATION LEAD

(75) Inventors: Timothy S. Jones, Carrollton, TX (US); Terry Daglow, Allen, TX (US); Peter B. Hegi, Dallas, TX (US); Thomas K. Hickman, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 639 days.

(21) Appl. No.: 12/098,007

(22) Filed: Apr. 4, 2008

(65) Prior Publication Data
US 2008/0188916 A1    Aug. 7, 2008

Related U.S. Application Data

(60) Division of application No. 11/119,438, filed on Apr. 29, 2005, now Pat. No. 7,359,755, which is a continuation-in-part of application No. 10/637,342, filed on Aug. 8, 2003, now abandoned.

(51) Int. Cl.
*A61N 1/04* (2006.01)
(52) U.S. Cl. ........ 607/117; 607/115; 607/116; 607/118; 604/164; 604/164.1; 604/171
(58) Field of Classification Search .......... 607/115–118; 604/164, 164.1, 171
See application file for complete search history.

(56) References Cited

U.S. PATENT DOCUMENTS

| | | | |
|---|---|---|---|
| 4,306,562 A | 12/1981 | Osborne | |
| 4,512,351 A * | 4/1985 | Pohndorf | 607/117 |
| 4,573,448 A | 3/1986 | Kambin | |
| 4,629,450 A | 12/1986 | Suzuki et al. | |
| 4,950,257 A | 8/1990 | Hibbs et al. | |
| 5,190,528 A * | 3/1993 | Fonger et al. | 604/171 |
| 5,255,691 A * | 10/1993 | Otten | 607/117 |
| 5,275,611 A | 1/1994 | Behl | |
| 5,300,032 A | 4/1994 | Hibbs et al. | |
| 5,725,504 A | 3/1998 | Collins | |
| 5,730,754 A | 3/1998 | Obenchain | |
| 5,779,715 A | 7/1998 | Tu | |
| 5,782,807 A | 7/1998 | Falvai | |
| 6,104,960 A | 8/2000 | Duysens et al. | |
| 6,169,916 B1 | 1/2001 | West | |

(Continued)

FOREIGN PATENT DOCUMENTS

EP    0972538    1/2000

(Continued)

*Primary Examiner* — Niketa Patel
*Assistant Examiner* — Rex R Holmes
(74) *Attorney, Agent, or Firm* — Craig Hoersten; Christopher S. L. Crawford; Melissa Acosta

(57) ABSTRACT

In one embodiment, an introducer is provided for implanting an electrical stimulation lead to enable electrical stimulation of nerve tissue. The introducer includes an outer sheath and an inner penetrator. The outer sheath may accommodate insertion of the electrical stimulation lead and may be inserted into a human body near the nerve tissue. The inner penetrator is removably housed within the outer sheath and includes an inner channel configured to accommodate a guide wire, a tip end having a shape and size substantially conforming to that of the guide wire, a body region having a shape and size substantially conforming to that of the outer sheath, and one or more transition regions substantially connecting the tip end with the body region. At least a portion of the transition regions of the inner penetrator may flex to substantially follow flexures in the guide wire during advancement of the inner penetrator.

15 Claims, 18 Drawing Sheets

U.S. PATENT DOCUMENTS

| | | |
|---|---|---|
| 6,249,707 B1 | 6/2001 | Kohnen et al. |
| 6,309,401 B1 * | 10/2001 | Redko et al. .................. 606/185 |
| 6,360,750 B1 | 3/2002 | Gerber et al. |
| 6,478,806 B2 | 11/2002 | McFarlane |
| 6,494,893 B2 | 12/2002 | Dubrul et al. |
| 6,512,958 B1 | 1/2003 | Swoyer et al. |
| 6,520,907 B1 | 2/2003 | Foley et al. |
| 6,530,902 B1 | 3/2003 | Jonkman |
| 6,714,822 B2 | 3/2004 | King et al. |
| 6,847,849 B2 | 1/2005 | Mamo et al. |
| 6,971,393 B1 | 12/2005 | Mamo et al. |
| 7,022,109 B1 | 4/2006 | Ditto |
| 7,359,755 B2 | 4/2008 | Jones et al. |
| 2002/0147485 A1 * | 10/2002 | Mamo et al. .................. 607/116 |
| 2003/0028147 A1 | 2/2003 | Aves et al. |
| 2003/0036787 A1 | 2/2003 | Redko et al. |
| 2004/0015133 A1 | 1/2004 | Karim |
| 2005/0033393 A1 | 2/2005 | Daglow et al. |
| 2005/0288758 A1 | 12/2005 | Jones et al. |
| 2005/0288759 A1 | 12/2005 | Jones et al. |

FOREIGN PATENT DOCUMENTS

| | | |
|---|---|---|
| WO | 03013650 | 2/2003 |

* cited by examiner

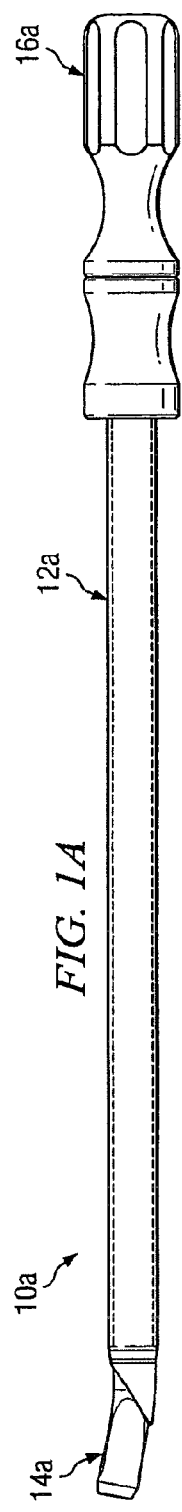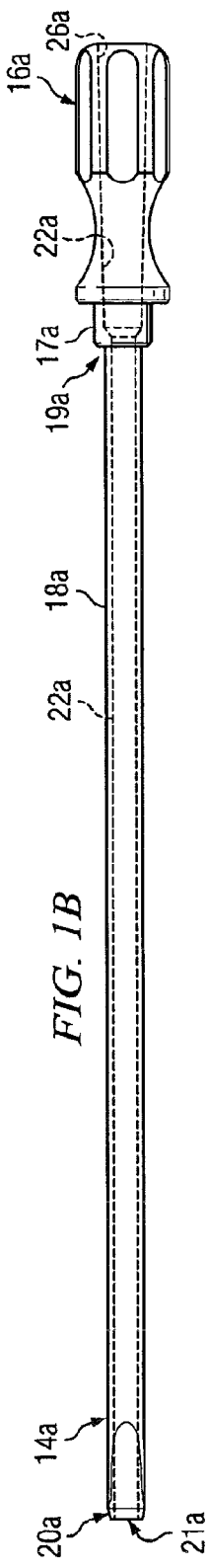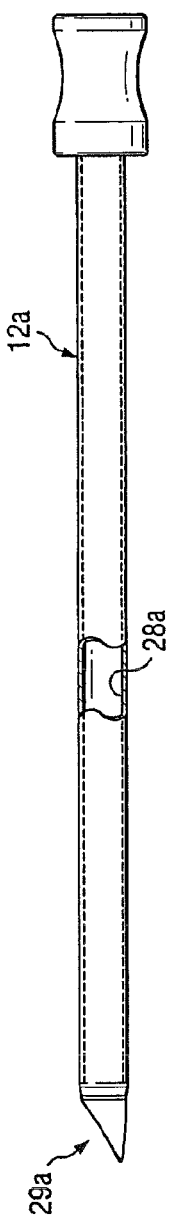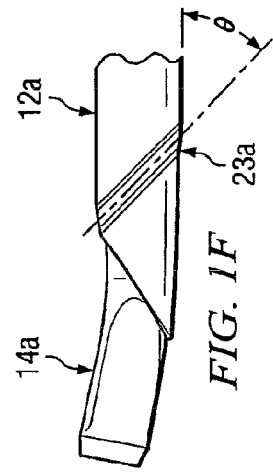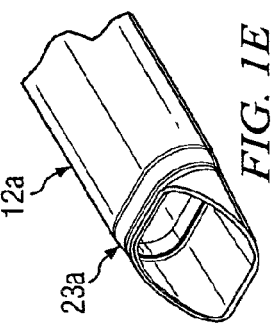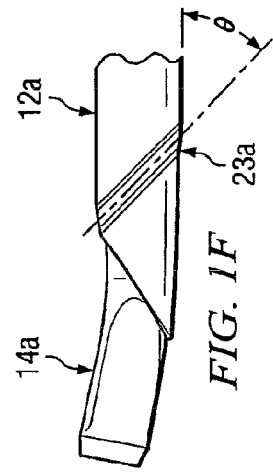

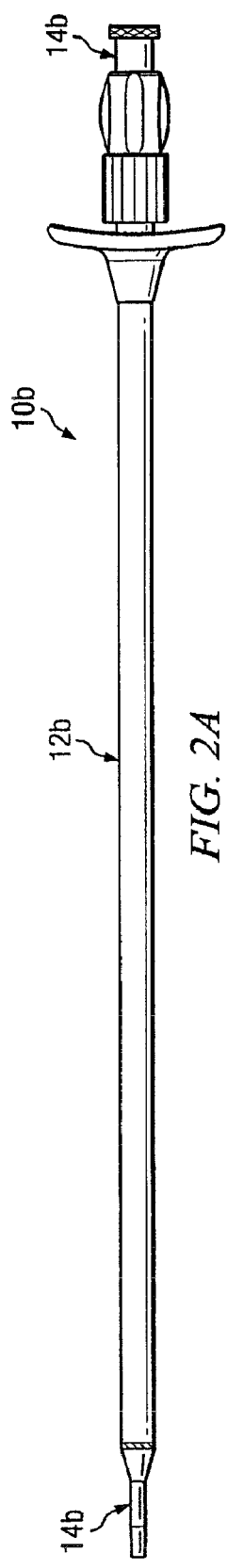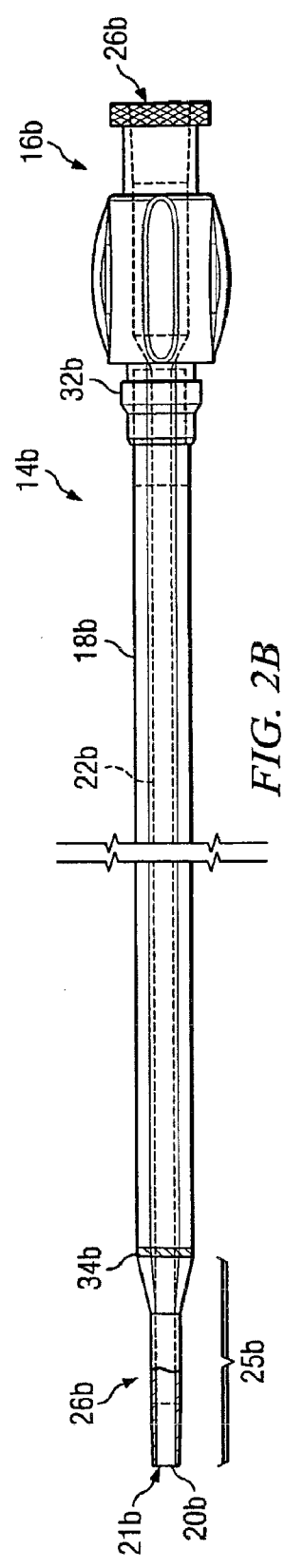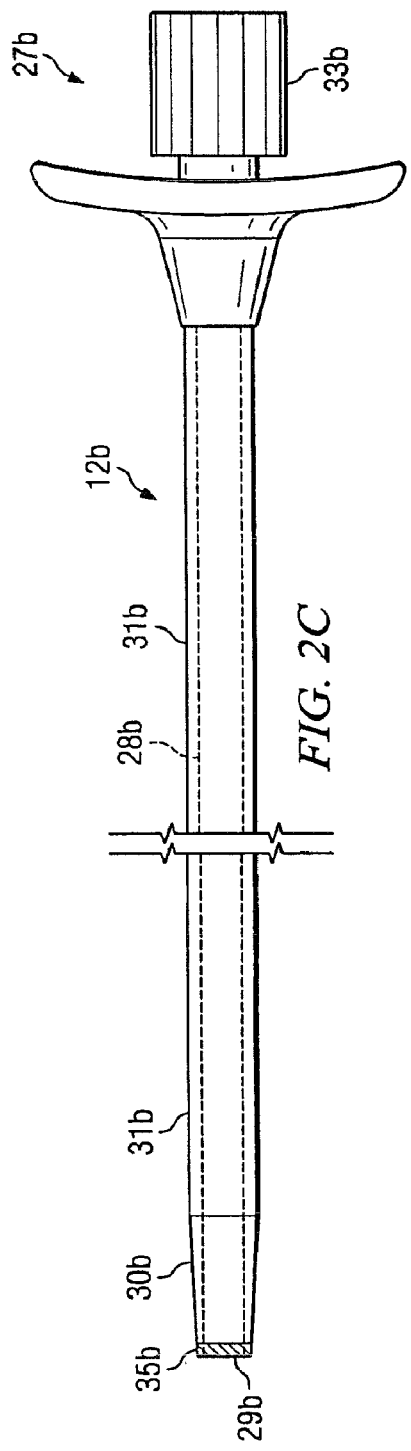

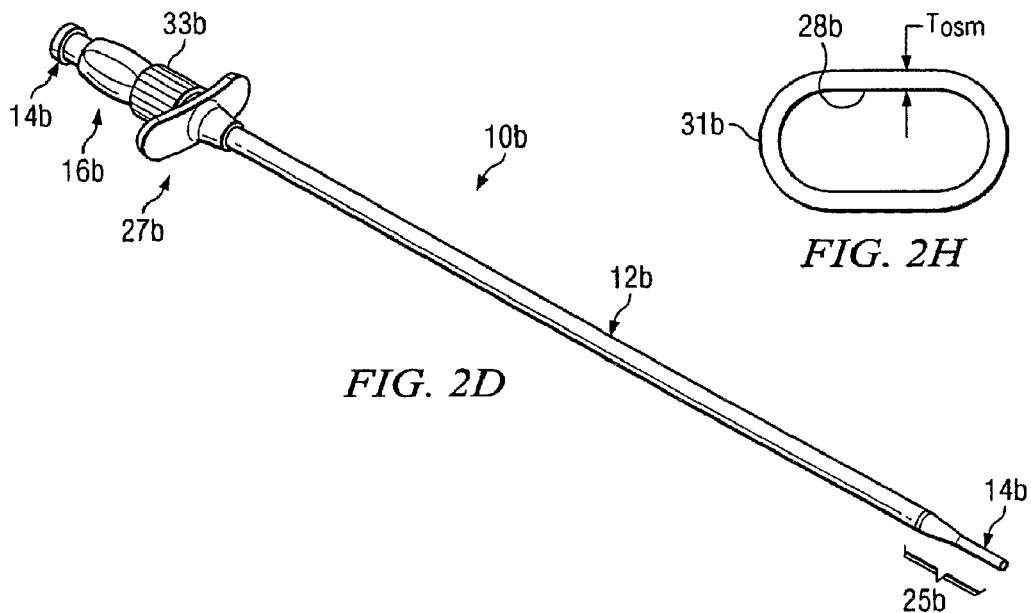
FIG. 2D
FIG. 2H
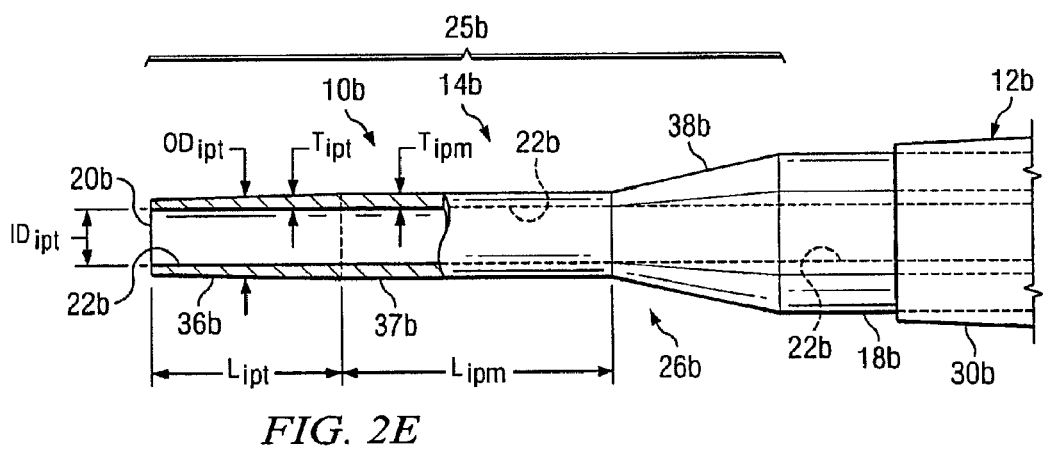
FIG. 2E
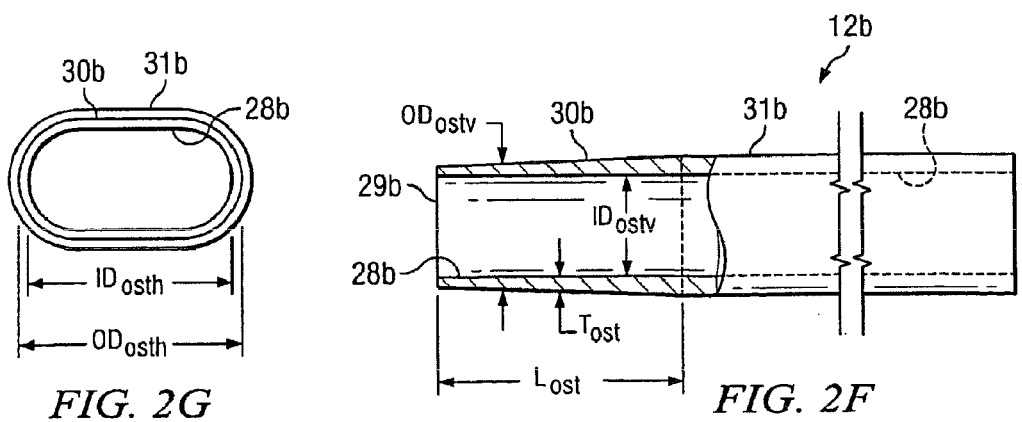
FIG. 2G
FIG. 2F

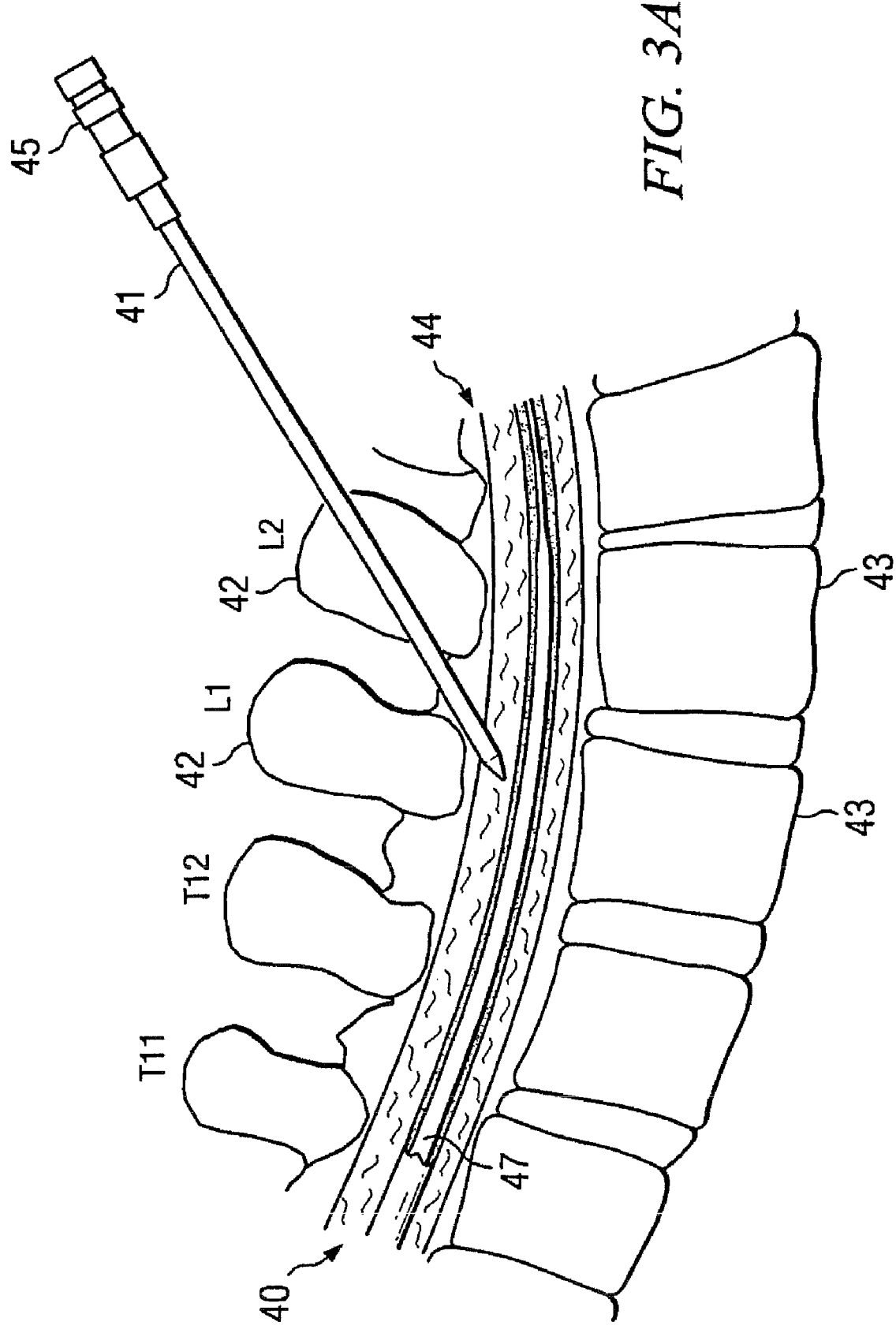

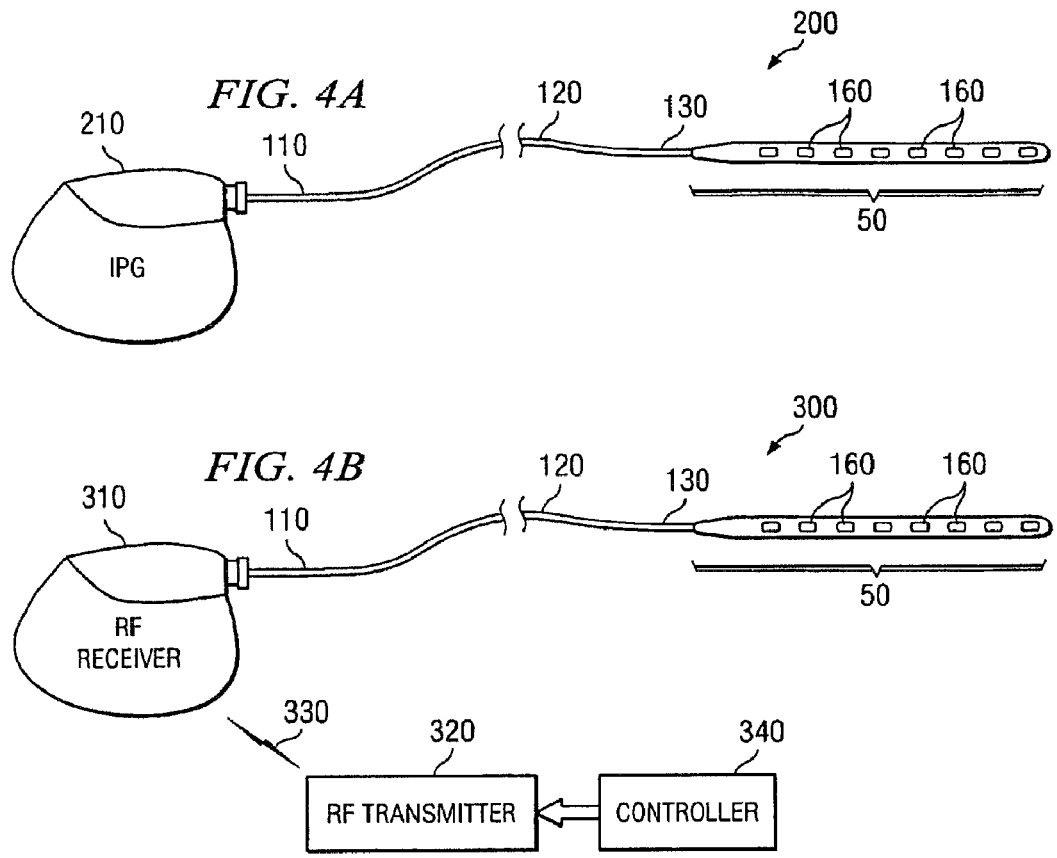
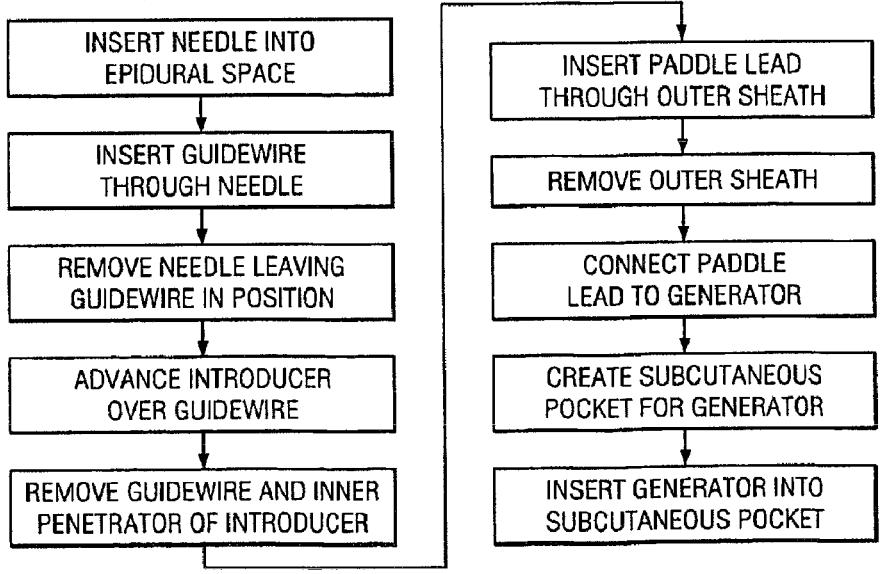

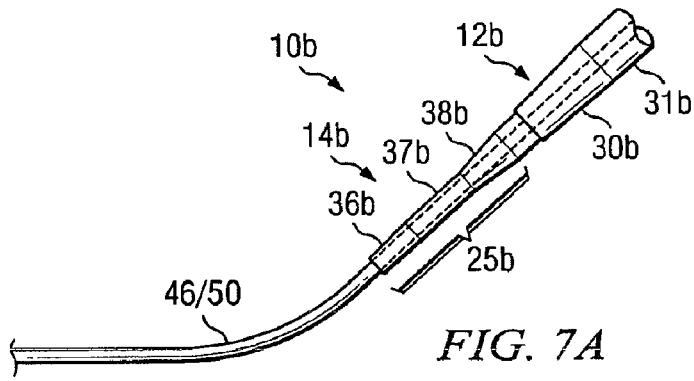
FIG. 7A
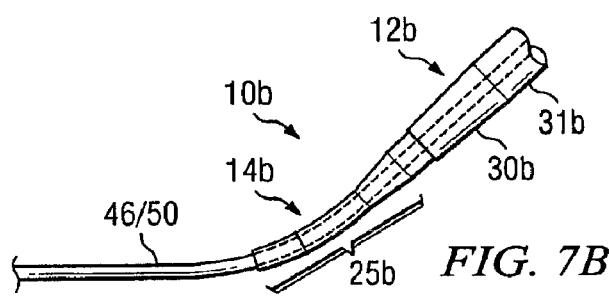
FIG. 7B
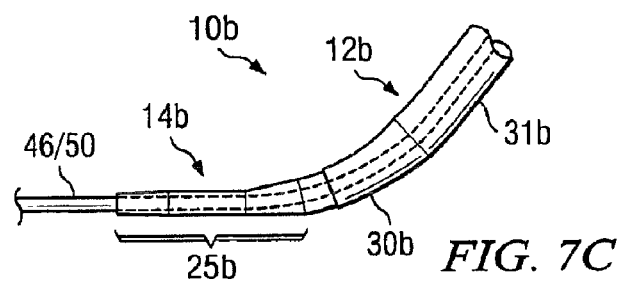
FIG. 7C
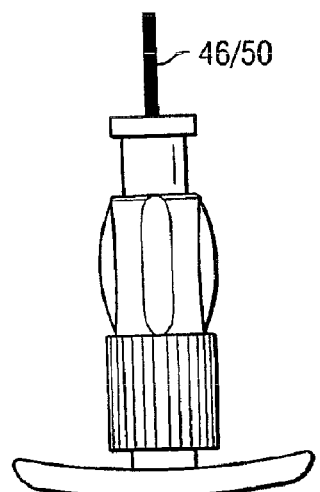
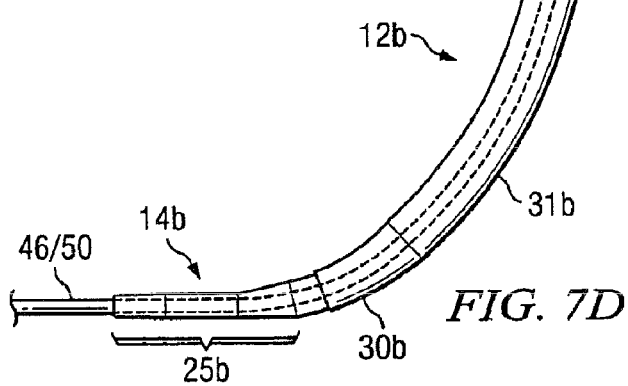
FIG. 7D

APPARATUS FOR IMPLANTING AN ELECTRICAL STIMULATION LEAD

CROSS-REFERENCE TO RELATED APPLICATIONS

This application is a divisional of U.S. application Ser. No. 11/119,438, filed Apr. 29, 2005, now Pat. No. 7,359,755, which is a continuation-in-part of U.S. application Ser. No. 10/637,342 filed Aug. 8, 2003 (now abandoned), the disclosures of which are fully incorporated herein by reference.

BACKGROUND

This invention relates generally to electrical stimulation leads for medical applications and in particular to a method and apparatus for implanting an electrical stimulation lead using a flexible introducer One method of delivering electrical energy is to implant an electrode and position it in a precise location adjacent the spinal cord such that stimulation of the electrode causes a subjective sensation of numbness or tingling in the affected region of the body, known as "paresthesia." Pain managing electrical energy is commonly delivered through electrodes positioned external to the dura layer surrounding the spinal cord. The electrodes may be carried by either of two primary vehicles: a percutaneous lead and a laminotomy or "paddle" lead.

Percutaneous leads commonly have three or more equally-spaced electrodes. They are positioned above the dura layer using a needle that is passed through the skin, between the desired vertebrae and onto the top of the dura. Percutaneous leads deliver energy radially in all directions because of the circumferential nature of the electrode. Percutaneous leads can be implanted using a minimally invasive technique. In a typical percutaneous lead placement, a trial stimulation procedure is performed to determine the optimal location for the lead. Here, a needle is placed through the skin and between the desired vertebrae. The percutaneous lead is then threaded through the needle into the desired location over the spinal cord dura. Percutaneous leads may also be positioned in other regions of the body near peripheral nerves for the same purpose.

Laminotomy or paddle style leads have a paddle-like configuration and typically possess multiple electrodes arranged in one or more independent columns. Paddle style leads provide a more focused energy delivery than percutaneous leads because electrodes may be present on only one surface of the lead. Paddle style leads may be desirable in certain situations because they provide more direct stimulation to a specific surface and require less energy to produce a desired effect. Because paddle style leads are larger than percutaneous leads, they have historically required surgical implantation through a procedure known as partial laminectomy that requires the resection and removal of vertebral tissue.

SUMMARY OF THE INVENTION

The present invention provides an introducer and process for implanting a paddle style electrical stimulation lead.

In one embodiment, an introducer is provided for implanting a paddle style electrical stimulation lead to enable electrical stimulation of nerve tissue. The introducer includes an outer sheath and an inner penetrator. The outer sheath may accommodate insertion of the paddle style electrical stimulation lead and may be inserted into a human body near the nerve tissue. The inner penetrator is removably housed within the outer sheath and includes an inner channel configured to accommodate a guide wire, a tip end having a shape and size substantially conforming to that of the guide wire, a body region having a shape and size substantially conforming to that of the outer sheath, and one or more transition regions substantially connecting the tip end with the body region. The inner penetrator may be advanced along the guide wire to a desired location relative to the nerve tissue and removed from the outer sheath leaving the outer sheath substantially in position for insertion of the paddle style electrical stimulation lead through the outer sheath into position proximate the nerve tissue. At least a portion of the transition regions of the inner penetrator may flex to substantially follow flexures in the guide wire during advancement of the inner penetrator along the guide wire.

In another embodiment, a method is provided for implanting a paddle style electrical stimulation lead to enable electrical stimulation of nerve tissue. The method includes inserting a needle into tissue, positioning a guide wire through the needle into a desired location relative to the nerve tissue, removing the needle, and forming a tract for the paddle style electrical stimulation lead by advancing an introducer along the guide wire to a desired location. The introducer includes an outer sheath and inner penetrator removably housed within the outer sheath, the inner penetrator including a tip end having a cross-sectional shape and size substantially conforming to a cross-sectional shape and size of the guide wire, a body region having a cross-sectional shape and size substantially conforming to a cross-sectional shape and size of the outer sheath, and one or more transition regions substantially connecting the tip end with the body region. At least a portion of the one or more transition regions flexes to substantially follow flexures in the guide wire during advancement of the inner penetrator along the guide wire. After advancing the introducer along the guide wire to the desired location, the inner penetrator is removed, leaving the outer sheath substantially in position, and the paddle style electrical stimulation lead is inserted through the outer sheath until the paddle style electrical stimulation lead is positioned proximate the nerve tissue.

In another embodiment, a method is provided for implanting an electrical stimulation lead in a minimally invasive percutaneous manner to enable electrical stimulation of a human's spinal nerve tissue. The method includes inserting a needle into the human's epidural space and inserting a guide wire through the needle until an end of the guide wire is positioned in the epidural space at a desired location relative to the spinal nerve tissue to be stimulated. The position of the guide wire in the epidural space is verified using fluoroscopy, and the needle is removed, leaving the guide wire substantially in position. An introducer is advanced along the guide wire until an end of the inner penetrator of the introducer is positioned in the epidural space at a desired location with respect to the spinal nerve tissue to be stimulated. The introducer includes an outer sheath and an inner penetrator removably housed within the outer sheath, the inner penetrator of the introducer including an inner channel configured to accommodate the guide wire, a tip end having a cross-sectional shape and size substantially conforming to a cross-sectional shape and size of the guide wire, a body region having a cross-sectional shape and size substantially conforming to a cross-sectional shape and size of the outer sheath, and one or more transition regions substantially connecting the tip end with the body region. as the inner penetrator of the introducer advances along the guide wire, at least one of the tip transition regions flexes to substantially follow flexures in the guide wire, and the outer sheath of the introducer forms a tract in the epidural space. The position of the introducer in the epidural space is verified using fluoroscopy. The guide wire and the inner penetrator of the introducer are removed, leaving the outer sheath of the introducer substantially in position. The electrical stimulation lead is inserted through the outer sheath of the introducer until the electrical stimulation lead is positioned in the epidural space proximate the spinal nerve tissue to be stimulated, and the positioning of the paddle style electrical stimulation lead in the epidural space is verified using fluoroscopy.

In another embodiment, a system for implanting a paddle style electrical stimulation lead to enable electrical stimulation of a human's spinal nerve tissue is provided. The system includes a needle, a guide wire, and an introducer. The introducer includes an outer sheath and an inner penetrator. The outer sheath is configured to accommodate insertion of the paddle style electrical stimulation lead through the outer sheath and may be inserted through the human's skin and into the human's epidural space. The inner penetrator is removably housed within the outer sheath and includes an inner channel configured to accommodate a guide wire, a tip end having a cross-sectional shape and size substantially conforming to a cross-sectional shape and size of the guide wire, a body region having a cross-sectional shape and size substantially conforming to a cross-sectional shape and size of the outer sheath, and one or more transition regions substantially connecting the tip end with the body region. The inner penetrator may be advanced along the guide wire until an end of the inner penetrator is positioned in the epidural space at a desired location relative Lo spinal nerve tissue to be stimulated, the outer sheath forming an insertion tract as the inner penetrator advances along the guide wire. A tip transition region of the inner penetrator is formed from a particular material and has a wall thickness sufficiently thin such that during advancement of the inner penetrator along the guide wire, the tip transition region may flex to substantially follow flexures in the guide wire. The inner penetrator is configured to be removed from the outer sheath leaving the outer sheath substantially in position for insertion of the paddle style electrical stimulation lead through the outer sheath into position proximate the spinal nerve tissue to be stimulated. The system also includes an implantable generator to power the paddle style electrical stimulation lead.

In another embodiment, a lead introducer kit for preparing to implant an electrical stimulation lead for electrical stimulation of nerve tissue is provided. The lead introducer kit includes a needle, a guide wire, a lead blank having a similar shape and size as an electrical stimulation lead to be inserted proximate the nerve tissue, and an introducer. The lead blank is configured for insertion into the human body to determine whether the electrical stimulation lead may be inserted into position proximate nerve tissue to be stimulated. The introducer includes an outer sheath and an inner penetrator. The outer sheath is operable to be inserted into a human body near nerve tissue to be stimulated. The inner penetrator is removably housed within the outer sheath and includes an inner channel configured to accommodate the guide wire. The inner penetrator is configured to be advanced along the guide wire to a desired location relative to the nerve tissue and removed from the outer sheath leaving the outer sheath substantially in position for insertion of the lead blank through the outer sheath to determine whether the electrical stimulation lead may be inserted into position proximate the nerve tissue to be stimulated.

In another embodiment, a method of removing an electrical stimulation lead from a human body is provided. A stimulation lead introducer is positioned over a body portion of an electrical stimulation lead that is at least partially implanted in a human body. The stimulation lead introducer includes an outer sheath and an inner penetrator removably housed within the outer sheath and comprising an inner channel, a tip region of the inner penetrator extending out from the outer sheath, the stimulation lead introducer being positioned such that the body portion of the electrical stimulation lead is partially disposed within an inner channel of the inner penetrator. The stimulation lead introducer is advanced along the body portion of the electrical stimulation lead until the tip region of the inner penetrator is located adjacent a stimulation portion of the electrical stimulation lead. The outer sheath is advanced relative to the inner penetrator until the outer sheath covers at least a portion of the stimulation portion of the electrical stimulation lead. The outer sheath, the inner penetrator, and the electrical stimulation lead are then removed from the human body.

Particular embodiments of the present invention may provide one or more technical advantages. For example, certain embodiments may allow a paddle style electrical stimulation lead to be inserted using a minimally invasive procedure, using an introducer, rather than a partial laminectomy or other more invasive surgical procedure. Certain embodiments may provide a guide wire, introducer and paddle style electrical stimulation lead composed in part or entirely of radio-opaque material to allow for fluoroscopic verification of the position of the guide wire, introducer and lead. Certain embodiments may provide an inner penetrator including a hollow tip configured to extend beyond the outer sheath, the tip having a raised circumferential ridge configured to create resistance when the circumferential ridge contacts the human's tissue. Other embodiments may provide a smooth transition between the inner penetrator and the outer sheath to prevent the introducer from getting caught or stuck in the tissue. Certain embodiments may provide an inner penetrator having a substantially flexible tip that may flex to maneuver around obstructions or physical structures in the body and/or to follow curvatures in a guide wire. Certain embodiments may provide a lead introducer kit including a lead blank that may be used to determine whether an actual electrical stimulation lead may be inserted into a desired position in the body. Thus, in situations where it is determined (using the lead blank) that the actual lead cannot be inserted into the desired position in the body, the actual lead not need to be removed from its packaging or inserted into the body, thus saving the actual lead for another use. Certain embodiments may provide a desirable method for removing an implanted electrical stimulation lead using a lead introducer having an outer sheath and in inner penetrator. Certain embodiments may provide all, some, or none of these advantages. Certain embodiments may provide one or more other technical advantages, one or more of which may be readily apparent to those skilled in the art from the figures, description and claims included herein.

BRIEF DESCRIPTION OF THE DRAWINGS

To provide a more complete understanding of the present invention and the features and advantages thereof, reference is made to the following description taken in conjunction with the accompanying drawings, in which:

FIG. 1A illustrates an example introducer for implanting a paddle style electrical stimulation lead according to one embodiment of the invention;

FIG. 1B illustrates an example inner penetrator of the introducer shown in FIG. 1A;

FIG. 1C illustrates an example of an outer sheath of the introducer shown in FIG. 1A;

FIG. 1D illustrates an example of a tip of the introducer shown in FIG. 1A;

FIG. 1E illustrates an example of a tip of the outer sheath of the introducer shown in FIG. 1A;

FIG. 1F illustrates a side view of an example of the tip of the introducer shown in FIG. 1A;

FIG. 2A illustrates an example introducer for implanting a paddle style electrical stimulation lead according to another embodiment of the invention;

FIG. 2B illustrates an example inner penetrator of the introducer shown in FIG. 2A;

FIG. 2C illustrates an example of an outer sheath of the introducer shown in FIG. 2A;

FIG. 2D illustrates a perspective view of the introducer shown in FIG. 2A;

FIG. 2E illustrates an example tip region of the inner penetrator shown in FIG. 2B;

FIGS. 2F-2H illustrate an example of a body portion and tip portion of the outer sheath shown in FIG. 2C;

FIG. 3A illustrates an example of a needle inserted into a human's epidural space;

FIG. 4A illustrates an example of a stimulation system;

FIG. 4B illustrates an example of a stimulation system; and

FIG. 5 is a flow chart describing steps for implanting a stimulation system;

FIGS. 7A-7D illustrate example views of a lead introducer flexing as it moves along a guide wire within the body according to certain embodiments of the invention;

DESCRIPTION OF EXAMPLE EMBODIMENTS

Figure 3B:
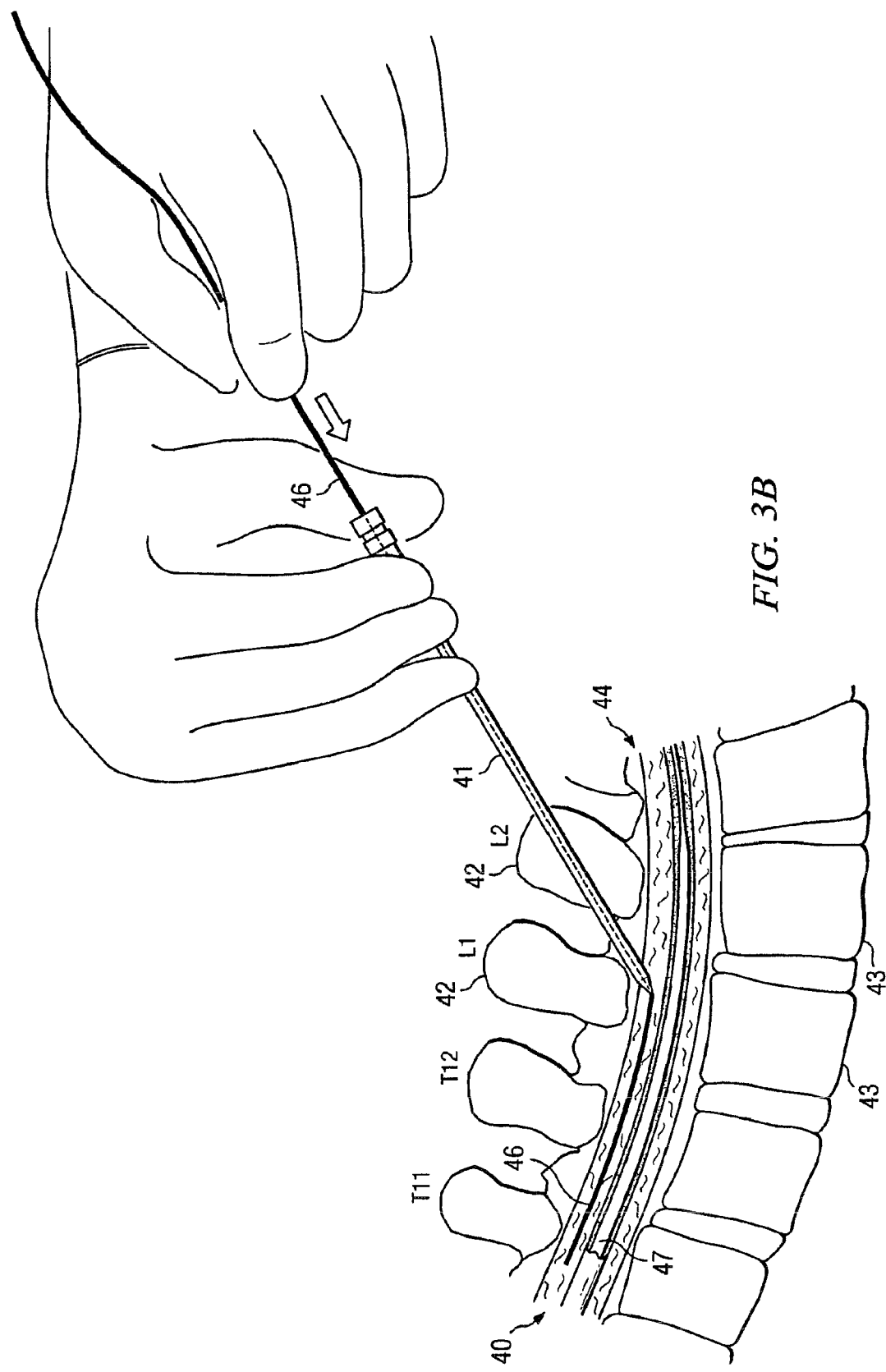
FIG. 3B illustrates an example of a guide wire being inserted through a needle into a human's epidural space.

FIG. 1A illustrates an example introducer 10a for implanting a paddle style electrical stimulation lead percutaneously according to one embodiment of the invention. Introducer 10a may be used to percutaneously introduce a percutaneous or paddle style lead into the epidural space of a user who requires electrical stimulation treatment directed to spinal nerve tissue, for example, for pain management. For example, and not by way of limitation, introducer 10a may be used to percutaneously introduce any of the percutaneous or paddle style leads shown and/or described in U.S. Publication No. 2002/0022873, filed on Aug. 10, 2001; U.S. Provisional Application No. 60/645,405, filed on Apr. 28, 2004; and/or U.S. Provisional Application No. 60/566,373, filed on Jan. 19, 2005. The same or an analogous, perhaps smaller, introducer 10a may be used to implant a percutaneous or paddle style lead into other tissue for electrostimulation treatment of a peripheral nerve. In one embodiment, introducer 10a includes an outer sheath 12a and an inner penetrator 14a.

FIG. 1B illustrates an example inner penetrator 14a disassembled from outer sheath 12a. Inner penetrator 14a includes handle 16a, connector 17a, and body 18a having proximal end 19a and distal end or tip 20a. Tip 20a may be tapered. Connector 17a connects handle 16a to body 18a. An inner channel 22a is formed through handle 16a and body 18a and connects opening 26a of handle 16a to opening 21a of tip 20a. Inner channel 22a may be configured to attach to a syringe. Inner channel 22a is wide enough to accommodate guide wires of various sizes along which introducer 10a may be advanced during use. Channel 22a may taper or otherwise decrease in diameter as it traverses connector 17a at the handle-body junction. Inner penetrator 14a may be formed from a plastic, such as silastic, HDPE or another polymer, or any other suitable material. Tip 20a of inner penetrator 14a may be curved as shown in FIGS. 1A-1C or may be curved into any other suitable shapes by an operator before inserting the introducer. In certain embodiments, inner penetrator 14a may be bent or curved into a suitable configuration to allow passage around an anatomical obstruction, or formed into any other shape suitable for particular anatomic regions of the body.

FIG. 1C illustrates outer sheath 12a disassembled from inner penetrator 14a. The lumen 28 of outer sheath 12a may range in width, for example from approximately 2 mm to approximately 6 mm. Lumen 28 may be oblong, oval, or substantially rectangular as needed to accommodate paddle style leads of various configurations. Outer sheath 12a may taper slightly at tip 29. Tip 29 of outer sheath 12a may be beveled to allow easier passage through tissue and to allow inner penetrator 14a to protrude out of tip 29.

In some embodiments, outer sheath 12a may be formed from a flexible material, such as a plastic or polymer, such as PEBAX, or any other suitable polyethylene type material, for example, such that outer sheath 12a may flex to follow a guide wire and/or to maneuver around obstructions or physical structures in the body. In other embodiments, outer sheath 12a may be formed from a more rigid material, such as a metal, such as stainless steel or titanium, or any other suitable material that is stiff and resists bending when outer sheath 12a is inserted through the paravertebral tissue and into the epidural space. In one embodiment, inner penetrator 14a includes tapered tip 20a shown in FIG. 1D. Tapered tip 20a protrudes out of outer sheath 12a. Tapered tip 20a preferably allows introducer 10a to pass easily over a guide wire without creating a false passage in an undesirable location in the tissue.

In one embodiment of outer sheath 12a, shown in FIGS. 1D-1F, tip 20a includes a raised circumferential shoulder or ridge 23a configured to provide an indication or "feel" to a physician as raised ridge 23a comes in contact with the ligamentum flavum. This "feel" occurs when raised ridge 23a comes in contact with the ligamentum flavum causing a slight resistance, pressure, or "notch" feel to the physician as raised ridge 23a comes in contact with and passes through the ligamentum flavum. As many physicians rely on "feel" while performing delicate procedures, this aspect may provide an important indication to the physician as to the location of outer sheath 12a and thus introducer 10a as a whole.

Such a raised ridge 23a can also be applied to needles or cutting devices that otherwise fail to provide physicians sufficient "feel" or a locative indication as the needle cuts through the ligamentum flavum. For example, the edge of outer sheath 12a in FIG. 1E could be configured into a cutting surface for a paddle insertion type needle. The improvement of raised ridge 23a on such a cutting device would provide the needed "feel" or indication to the physician as to where the needle was in the human tissue, thus providing confidence to the physician, as the physician uses such a large needle, that the needle has not yet entered the interthecal space.

Further, raised ridge 23a assists in spreading the fibers of the paravertebral muscle and ligaments as it is inserted. Raised ridge 23a may be angled to assist insertion, for example, at an angle of thirty-five to forty-five degrees or any other angle that would facilitate passage of outer sheath through tissue. During insertion, raised ridge 23a ultimately makes contact with the ligamentum flavum and rests against it during insertion of a guide wire and an electrical stimulation lead.

As shown in FIGS. 1D and 1E, in some embodiments, outer sheath 12a, lumen 28a, and inner penetrator 14a may have oblong, oval, or substantially rectangular cross-sections as needed to accommodate paddle style leads of various configurations. Such configuration also prevents inner penetrator 14a from rotating within lumen 28a of outer sheath 12a, which may be advantageous for inserting a lead into the target region in the body. For example, such configuration that prevents the rotation of inner penetrator 14a within lumen 28a may allow an operator to ensure that the lead is facing in the desired direction. In addition, a non-circular cross-section may provide additional flexibility to introducer 10, which may be advantageous for navigating into particular regions in the body, such as the epidural region, for example.

In one embodiment, outer sheath 12a, inner penetrator 14a, or both may be formed from radio-opaque material or may include radio-opaque markers that allow the position of outer sheath 12a, inner penetrator 14a, or both to be visualized with fluoroscopy or plain x-rays, for example, during the insertion process to insure proper positioning in the epidural space.

FIG. 2A illustrates another example introducer 10b for implanting a paddle style electrical stimulation lead percutaneously according to another embodiment of the invention. Introducer 10b may be used to percutaneously introduce a percutaneous or paddle style lead into the epidural space of a user who requires electrical stimulation treatment directed to nerve tissue (e.g., spinal nerve tissue), for example, for pain management. The same or an analogous, perhaps smaller, introducer 10b may be used to implant a percutaneous or paddle style lead into other tissue for electrostimulation treatment of a peripheral nerve. Like introducer 10a, introducer 10b may include an outer sheath 12b and an inner penetrator 14b.

FIG. 2B illustrates an example inner penetrator 14b disassembled from outer sheath 12b. Inner penetrator 14b includes a handle portion 16b, a body portion 18b, a distal or tip end 20b, and a tip portion 25b connecting body portion 18b with a tip end 20b. Tip portion 25b may include one or more transition regions 26b, which may provide a transition between the cross-sectional shape and size of body portion 18b and the cross-sectional shape and size of tip end 20b, as discussed in greater detail with reference to FIG. 2D. For example, one or more transition regions 26b may be tapered. Handle portion 16b may include an inner penetrator locking device 32b, which may interact with a locking device of outer sheath 12b (discussed below regarding FIG. 2C) in order to lock inner penetrator 14b in position within outer sheath 12b. However, any other type of handle known to those in the art may also be used.

An inner channel 22b is formed through handle portion 16b, body portion 18b, and tip portion 25b to connect an opening 26b in handle portion 16b with an opening 21b in tip end 20b. Inner channel 22b may be configured to attach to a syringe at a lure lock located at handle portion 16b or through another opening. Inner channel 22b may be configured to accommodate guide wires of various sizes along which introducer 10b may be advanced during use. In this embodiment, the diameter of inner channel 22b tapers proximate handle portion 16b, remains constant along the length of body portion 16b, and tapers slightly proximate tip region 25b. However, in other embodiments, inner channel 22b may not include a tapered portion. Inner penetrator 14b may be formed from a plastic, such as silastic, HDPE or another polymer, or any other suitable material. In addition, in some embodiments, the shape of inner penetrator 14b may be configured to facilitate steering of inner penetrator 14b. For example, one or more indentions, notches, or score lines may be formed in inner penetrator 14b to increase the flexibility and steerability of inner penetrator 14b.

FIG. 2C illustrates outer sheath 12b disassembled from inner penetrator 14b. Outer sheath 12b includes a handle portion 27b, a body portion 31b, a tip portion 30b, and a tip end 29b through which inner penetrator 14b may protrude, such as shown in FIGS. 2A and 2D. The inner channel, or lumen, 28b of outer sheath 12b may range in width, for example from approximately 2 mm to approximately 6 mm. In some embodiments, the cross-section of lumen 28b may be oblong, oval, or substantially rectangular as needed to accommodate paddle style leads of various configurations. The outer surface of outer sheath 12b may have a similar cross-section as lumen 28b. Thus, for example, the outer surface of outer sheath 12b may have an oblong, oval, or substantially rectangular cross-section. In some embodiments, outer sheath 12b, lumen 28b, and inner penetrator 14b may have oblong, oval, or substantially rectangular cross-sections as needed to accommodate paddle style leads of various configurations. As discussed above regarding introducer 10a, such configuration may prevent inner penetrator 14b from rotating within lumen 28b of outer sheath 12b, which may be advantageous for inserting and/or navigating a lead into the target region in the body. Outer sheath 12b may taper slightly proximate tip end 29b, which may be beveled to be substantially flush against the outer surface of inner penetrator 14b to allow easier passage through tissue, as discussed below.

In some embodiments, outer sheath 12b is formed from a plastic or polymer material, or any other suitable material that allows flexing when outer sheath 12b is inserted through certain tissue, such as the paravertebral tissue and into the epidural space, for example. In a particular embodiment, both outer sheath 12b and inner penetrator 14b are formed from plastic or polymer materials, but inner penetrator 14b is more flexible than outer sheath 12b due to the particular materials used to form outer sheath 12b and inner penetrator 14b and/or the size, wall thickness, or other dimensions of outer sheath 12b and inner penetrator 14b. In other embodiments, outer sheath 12b is formed from substantially rigid material, such as a metal, such as stainless steel or titanium, or any other suitable material that is stiff and resists flexing when outer sheath 12b is inserted through the paravertebral tissue and into the epidural space.

Handle portion 27b may include an outer sheath locking device 33b, which may interact with inner penetrator locking device 32b shown in FIG. 2B in order to lock inner penetrator 14b in position within outer sheath 12b. Inner penetrator locking device 32b and outer sheath locking device 33b may include any devices suitable to interact to lock inner penetrator 14b within outer sheath 12b. For example, locking devices 32b and 33b may include threaded portions such that inner penetrator 14b and outer sheath 12b may be locked and unlocked by rotation of at least one of locking devices 32b and 33b. As another example, locking devices 32b and 33b may snap together to lock inner penetrator 14b within outer sheath 12b. Locking inner penetrator 14b within outer sheath 12b may prevent outer sheath 12b from sliding down over inner penetrator 14b, which may damage tissue in the body or cause other problems. However, some embodiments do not include a locking mechanism.

In some embodiments, inner penetrator 14b and/or outer sheath 12b may be partially or completely formed from one or more materials that may be detected by one or more medical imaging techniques, such as ultrasound, fluoroscopy, MRI, fMRI and/or X-ray, such that the location of the inner penetrator 14b and/or outer sheath 12b within the human body may be determined. For example, inner penetrator 14b and/or outer sheath 12b may be formed from or doped with a radio-opaque material, such as barium sulphate ($BaSO_4$), for example. As another example, inner penetrator 14b and/or outer sheath 12b may include markers that may be detected by one or more of such medical imaging techniques. As shown in FIGS. 2B and 2C, inner penetrator 14b may include a first radio-opaque marker 34b and outer sheath 12b may include a second radio-opaque marker 35b. The location of inner penetrator 14b relative to outer sheath 12b may be determined based on the determined relative location of markers 34b and 35b. In addition, first and second radio-opaque markers 34b and 35b may have different radiopacity such that markers 34b and 35b may be distinguished from each other.

FIG. 2D illustrates a perspective view of introducer 10b. In this configuration, inner penetrator 14b may be locked within outer sheath 12b by locking devices 32b and 33b. Tip portion 25b of inner penetrator 14b protrudes through tip end 29b of outer sheath 12b. As discussed below with reference to FIGS. 3A-3F, inner penetrator 14b may be configured to be advanced along a guide wire to a desired location relative to particular nerve tissue to be stimulated and removed from outer sheath 12b, leaving outer sheath 12b substantially in position for insertion of an electrical stimulation lead through outer sheath 12b into position proximate the nerve tissue to be stimulated. Tip portion 25b of inner penetrator 14b may be sufficient to flex to substantially follow flexures (such as bends or curves) in the guide wire during advancement of inner penetrator 14b along the guide wire. In order to provide such flexibility, tip portion 25b may be formed from particular flexible materials and may have sufficiently thin walls, as discussed below with reference to FIG. 2E. In addition, as discussed above, outer sheath 12b may be formed from flexible materials and may have sufficiently thin walls in order to provide some flexibility of introducer 10b.

FIG. 2E illustrates a partial detailed view of body portion 18b and tip portion 25b of inner penetrator 14b, as well as a portion of tip portion 30b of outer sheath 12b, of introducer 10b. In this embodiment, tip portion 25b of inner penetrator 14b includes three transition regions 26b, which may provide a transition between the cross-sectional shape and size of body portion 18b and the cross-sectional shape and size of tip end 20b. Transition regions 26b include a tip transition region 36b, a middle transition region 37b, and a body transition region 38b. Tip transition region 36b has a substantially circular cross-section extending along the length of tip transition region 36b and tapering slightly toward tip end 20b. Middle transition region 37b has a substantially circular and constant cross-section along the length of middle transition region 37b. Thus, in this embodiment, middle transition region 37b is not tapered. Body transition region 38b has a cross-section that transitions from the cross-section of body portion 18b, which may substantially match the cross-section of lumen 28b of outer sheath 12b. In a particular embodiment, body transition region 38b transitions from a substantially oval cross-section adjacent body portion 18b to a substantially circular cross-section adjacent middle transition region 37b. Body transition region 38b may have a more severe taper than tip transition region 36b.

The materials and dimensions of one or more of tip transition region 36b, middle transition region 37b, and body transition region 38b may be selected to provide substantial flexibility to tip region 25b such that inner penetrator 14b may flex around particular features in the body, and such that when the inner penetrator 14b is advanced along a guide wire, tip regions 25b may flex to substantially follow flexures in the guide wire such that the guide wire is not significantly displaced by the advancing tip region 25b of inner penetrator 14b.

For example, the wall thickness of tip transition region 36b, denoted as thickness "$T_{ipt}$," may decrease toward tip end 20b. In some embodiments, the wall thickness $T_{ipt}$ of tip transition region 36b is less than or approximately equal to 0.02 inches at its thickest point along tip transition region 36b. The wall thickness $T_{ipt}$ of tip transition region 36b may be less than 0.01 inches at tip end 20b. In a particular embodiment, the wall thickness $T_{ipt}$ is approximately 0.006 inches at tip end 20b. The decreased wall thickness, $T_{ipt}$, of tip transition region 36b toward tip end 20b may provide for increased flexibility of tip transition region 36b. In addition, as shown in FIG. 2E, both the inner diameter, denoted as "$ID_{ipt}$," and the outer diameter, denoted as "$OD_{ipt}$," of tip transition region 36b may decrease or taper toward tip end 20b. The tapered outer diameter $OD_{ipt}$ and reduced wall thickness, $T_{ipt}$, of tip transition region 36b at tip end 20b may provide a relatively smooth transition between tip end 20b and a guide wire extending through tip opening 21b. Such smooth transition may reduce or eliminate the likelihood of the juncture between tip end 20b and a guide wire getting stuck or caught up, or pushing tissue forward, as inner penetrator 14b is advanced within the body.

The tapered inner diameter $ID_{ipt}$ may provide for a tight or close fit at tip end 20b with a guide wire running through opening 22b of inner penetrator 14b. In some embodiments, the tapered inner diameter $ID_{ipt}$ provides for an interference fit between inner penetrator 14b and a guide wire, at least at tip end 20b of inner penetrator 14b.

In addition, the length of tip transition region 36b, denoted as length "$L_{ipt}$," compared to wall thickness $T_{ipt}$, inner diameter ID and/or outer diameter OD, may be selected to provide desired flexibility of tip transition region 36b. For example, the ratio of the length $L_{ipt}$ to wall thickness $T_{ipt}$ at the thickest point may be greater than or approximately equal to 20 to 1. As another example, the ratio of the length $L_{ipt}$ to outer diameter $OD_{ipt}$ may be greater than or approximately equal to 2.5 to 1. Such configuration and dimensions may provide desired flexibility for tip transition region 36b.

The wall thickness of middle transition region 37b, denoted as thickness "$T_{ipm}$," which remains substantially constant along the length of middle transition region 37b, may be less than or approximately equal to 0.02 inches. In a particular embodiment, wall thickness $T_{ipm}$ is approximately 0.010 inches. Such configuration and dimensions may provide desired flexibility for middle transition region 37b.

In addition, the length of middle transition region 37b, denoted as length "$L_{ipm}$," compared to wall thickness $T_{ipm}$, the inner diameter and/or the outer diameter of middle transition region 37b, may be selected to provide desired flexibility of middle transition region 36b. For example, the ratio of the length $L_{ipm}$ to wall thickness $T_{ipm}$ may be greater than or approximately equal to 30 to 1. As another example, the ratio of the length $L_{ipm}$ to the outer diameter of middle transition region 37b may be greater than or approximately equal to 3 to 1. Such configuration and dimensions may provide desired flexibility for middle transition region 37b.

The total length of tip transition region 36b and middle transition region 37b ($L_{ipt}+L_{ipm}$) compared to the wall thickness at the thickest point along transition regions 36b and 37b or compared to the inner diameter and/or the outer diameter of middle transition region 37b, may be selected to provide desired flexibility of middle transition region 36b. For example, the ratio of the total length of tip transition region 36b and middle transition region 37b ($L_{ipt}+L_{ipm}$) to the wall thickness $T_{ipm}$ may be greater than or approximately equal to 40 to 1. As another example, the ratio of the total length of tip transition region 36b and middle transition region 37b ($L_{ipt}+L_{ipm}$) to the outer diameter of middle transition region 37b may be greater than or approximately equal to 5 to 1. Such configuration and dimensions may provide desired flexibility for tip portion 25b of inner penetrator 14b. The relatively long nose provided by tip transition region 36b and middle transition region 37b may provide more flexibility than a tip having a substantially uniform taper from body portion 18b to the tip end 20b of inner penetrator 14b, which flexibility may be desirable for navigating inner penetrator 14b along a guide wire, for example.

Although the embodiment shown in FIG. 2E includes three transition regions 26b, it should be understood that other embodiments may include more or less than three transition regions 26b (which may or may not include one or more transition regions 26b similar to transition regions 36b, 37b and/or 38b shown in FIG. 2E), or zero transition regions 26b.

In the embodiment shown in FIG. 2E, when inner penetrator 14b is fully advanced within (and/or locked together with) outer sheath 12b, a portion of the body portion 18b of inner penetrator 14b may protrude out through tip end 29b of outer sheath 12b. As discussed below, tip portion 30b of outer sheath 12b may be tapered to provide a relatively smooth transition between tip end 29b and body portion 18b of inner penetrator 14b protruding through tip end 29b. In other embodiments, body portion 18b of inner penetrator 14b may not protrude through tip end 29b of outer sheath 12b when inner penetrator 14b is fully advanced within (and/or locked together with) outer sheath 12b. In one embodiment, tip end 29b may substantially align with the intersection of body portion 18b and body transition region 38b of inner penetrator 14b.

FIGS. 2F-2H illustrates a detailed view of body portion 31b and tip portion 30b of outer sheath 12b of introducer 10b in accordance with one embodiment of the invention. In particular, FIG. 2F is a partial side view of outer sheath 12b, FIG. 2G is an end view of outer sheath 12b, and FIG. 2H is a cross-sectional view taken along the length of body portion 31b of outer sheath 12b.

Body portion 31b has a substantially oval or oblong cross-section extending along the length of body portion 31b. Tip portion 30b has a substantially oval or oblong cross-section that tapers in the direction from the end adjacent body portion 31b toward tip end 29b. The cross-section of lumen 28b at the tip end 29b of outer sheath 12b may substantially conform to the exterior cross-section of body portion 18b of inner penetrator 14b.

In some embodiments, the materials and dimensions of body portion 31b and/or tip portion 30b of outer sheath 12b may be selected to provide some degree of flexibility to outer sheath 12b such that outer sheath 12b may flex around particular features in the body, and such that when introducer 10b is advanced along a guide wire, outer sheath 12b (along with inner penetrator 14b) may flex to substantially follow curvatures in the guide wire such that the guide wire is not significantly displaced by the advancing introducer 10.

For example, as shown in FIG. 2F, the wall thickness of tip portion 30b, denoted as thickness "$T_{ost}$," which may be substantially uniform around the cross-sectional perimeter of tip portion 30b, may decrease toward tip end 29b. In some embodiments, the wall thickness $T_{ost}$ of tip portion 30b is less than or approximately equal to 0.03 inches at its thickest point along tip portion 30b and/or less than 0.02 inches at tip end 29b. In a particular embodiment, the wall thickness $T_{ost}$ is between approximately 0.007 inches and approximately 0.018 inches around the cross-sectional perimeter at tip end 29b. The decreased wall thickness, $T_{ost}$, of tip portion 30b toward tip end 29b may provide for increased flexibility of tip portion 30b.

In addition, as shown in FIG. 2F, the perimeter and/or cross-sectional area of lumen 28b may decrease or taper toward tip end 29b. In particular, in embodiments in which outer sheath 12b, including tip portion 30b, has an oval or oblong cross-section (such as shown in FIGS. 2G and 2H), both the horizontal inner diameter "$ID_{osth}$" and the horizontal outer diameter, "$OD_{osth}$" of tip portion 30b, and both the vertical inner diameter "$ID_{stv}$" and the vertical outer diameter "$OD_{ostv}$" of tip portion 30b may decrease or taper toward tip end 29b. The terms "horizontal" and "vertical" are used merely for illustrative purposes of FIGS. 2F-2G, as outer sheath 12b may be positioned in any orientation.

The tapered outer diameters $OD_{osth}$ and $OD_{ostv}$ and reduced wall thickness, $T_{ost}$, at tip end 29b may provide a relatively smooth transition between tip end 29b and body portion 18b of inner penetrator 14b (better illustrated in FIG. 2E). Such smooth transition may reduce or eliminate the likelihood of the juncture between outer sheath 12b and inner penetrator 14b getting stuck or caught up, or pushing tissue forward, as introducer 10b is advanced within the body.

The tapered lumen 28b (e.g., tapered inner diameters $ID_{osth}$ and $ID_{ostv}$) may provide for a tight or close fit at tip end 29b of outer sheath 12b with the outer surface of body portion 18b of inner penetrator 14b, such that inner penetrator 14b may be held substantially in place by outer sheath 12b. In some embodiments, the tapered lumen 28b provides for an interference fit between outer sheath 12b and inner penetrator 14b, at least at tip end 29b of outer sheath 12b.

In addition, the length of tip portion 30b, denoted as length "$L_{ost}$," compared to wall thickness $T_{ost}$, inner diameters $ID_{osth}$ and $ID_{ostv}$ and/or outer diameters $OD_{osth}$ and $OD_{ostv}$, may be selected to provide desired flexibility of tip portion 30b. For example, the ratio of the length $L_{ost}$ to wall thickness $T_{ost}$ at the thinnest point may be greater than or approximately equal to 10 to 1. Such configuration and dimensions may provide desired flexibility for tip portion 30b.

The wall thickness of body portion 31b, denoted as thickness "$T_{osm}$," which remains substantially constant along the length of body portion 31b, may be less than or approximately equal to 0.03 inches. In a particular embodiment, wall thickness $T_{osm}$ is approximately 0.024 inches. Such configuration and dimensions may provide desired flexibility for middle transition region 37b.

FIGS. 3A-3F illustrate an example method of implanting a paddle style electrical stimulation lead into a human's epidural space using an example introducer 10 (such as introducer 10a or introducer 10b, for example). Spinal cord 47 is also shown. A location between two vertebrae is selected for the procedure. The site may be selected using fluoroscopy. The first step in performing the procedure is to insert needle 41, preferably at an angle, into the skin, and through the subcutaneous tissue and ligamentum flavum 44 of the spine, and into a human's epidural space 40. In one embodiment of the method, for example, the introducer might be inserted at an angle of approximately thirty-five to approximately forty-five degrees. FIG. 3A illustrates insertion of needle 41 through the skin between spinous processes 42 of two vertebrae 43. Entry into epidural space 40 by needle 41 may be confirmed using standard methods such as the "loss-of-resistance" technique after stylet 45, or inner portion of needle 41, is removed.

After removing stylet 45 from needle 41, guide wire 46 may be inserted through needle 41 into epidural space 40, shown in FIG. 3B. A guide wire is used in a preferred embodiment of the method of insertion but is not required to insert a paddle style lead through the introducer. This part of the procedure may be performed under fluoroscopic guidance for example. Fluoroscopy may be used to check the position of guide wire 46 in epidural space 40 before inserting introducer 10. In some embodiments, a removable stylet may be inserted into a channel extending within and along the length of guide wire 46 and manipulated by the operator in order to help steer guide wire 46 into position. The stylet may also provide additional rigidity to guide wire 46, which may be desired in particular applications. Once the tip of guide wire 46 is in position within epidural space 40, needle 41 is removed. If a stylet was inserted into guide wire 46 as discussed above, the stylet may or may not be removed. For example, the stylet may be left in guide wire 46 in order to increase the rigidity or strength of guide wire 46 in order to resist guide wire 46 being moved by the advancement of introducer 10, as discussed below.

Figure 3C:
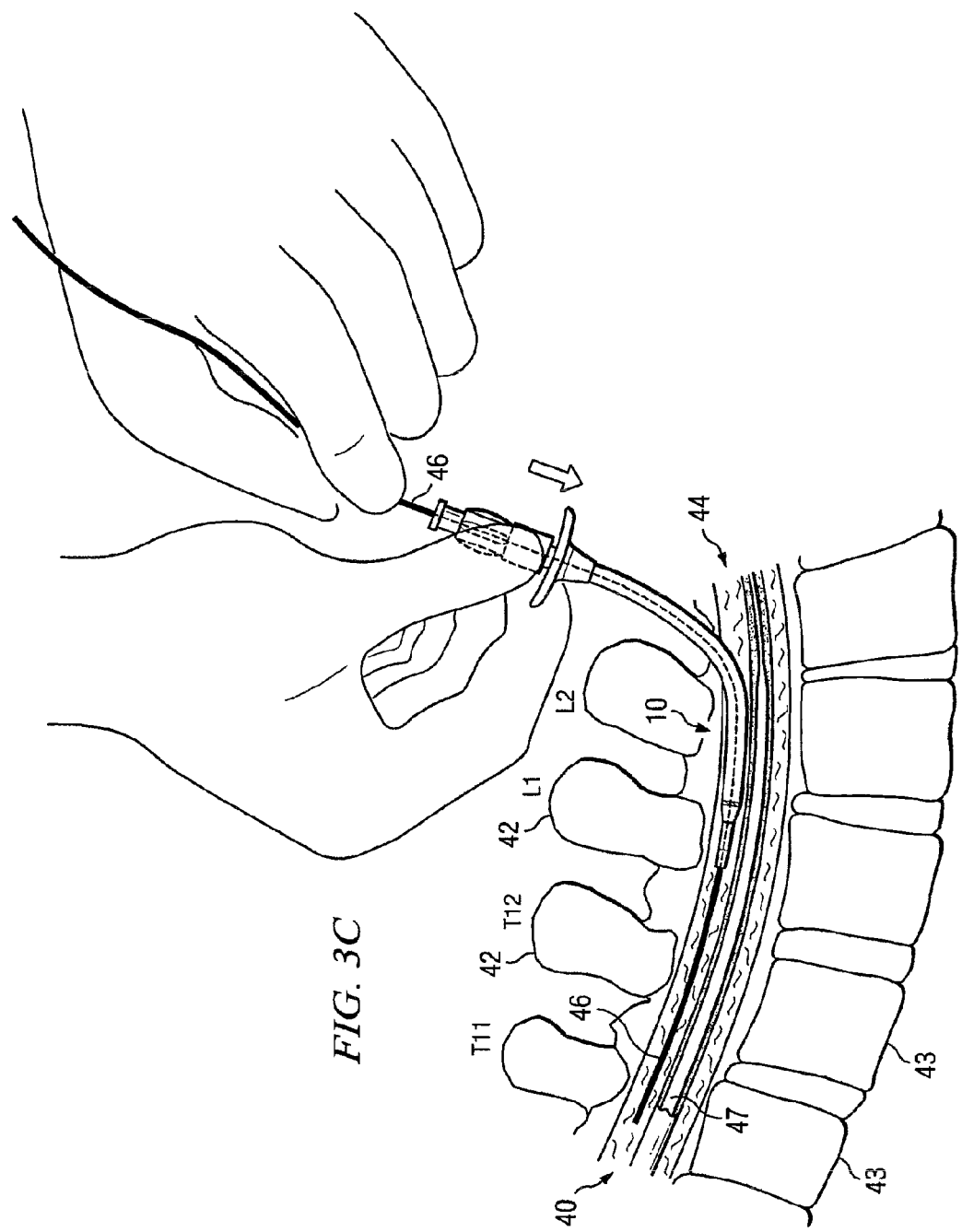
FIG. 3C illustrates an example of an introducer being inserted over a guide wire into a human's epidural space.

As shown in FIG. 3C, introducer 10 may then be inserted, preferably at an angle of approximately thirty-five to approximately forty-five degrees, although the exact angle may differ depending on technique and a patient's anatomy, over guide wire 46 and into epidural space 40 using guide wire 46 as a guide. The technique of passing introducer 10 over guide wire 46 helps ensure proper placement of introducer 10 into epidural space 40 and helps avoid inadvertent passage of introducer 10 into an unsuitable location. The operator may choose to cut the skin around the insertion site with a scalpel to facilitate subsequent entry of introducer 10 through the needle entry site. As discussed above, a stylet within guide wire 46 may increase the rigidity of guide wire 46 to resist guide wire 46 being moved or dislocated by introducer 10 as introducer 10 advances along guide wire 46. In some embodiments, as introducer 10 advances along flexures in guide wire 46, the tip of inner penetrator 14 and/or all or portions of outer sheath 12 may flex to maneuver around obstructions or physical structures in the body (such as a spinous process 42, vertebrae 43, or any other structure in the body) and/or to substantially follow curvatures in guide wire 46, rather than displacing portions of guide wire 46, which may cause damage to the body. An example of such flexing is shown and discussed below with reference to FIGS. 7A-7D.

As introducer 10 is passed through the skin it elongates the hole in the skin made by needle 41. As introducer 10 is passed deeper into the paravertebral tissues, it spreads the fibers of tissue, muscle and ligamentum flavum 44 and forms a tract through these tissues and into epidural space 40, preferably without cutting the tissues. At the level in the tissues where introducer 10 meets and penetrates ligamentum flavum 44 there is a second loss of resistance when inner penetrator 14 has completely penetrated the ligamentum flavum 44. Shoulder or ridge 23 of outer sheath 12 is preferably lodged against ligamentum flavum 44 during insertion of a paddle style lead.

Figure 3D:
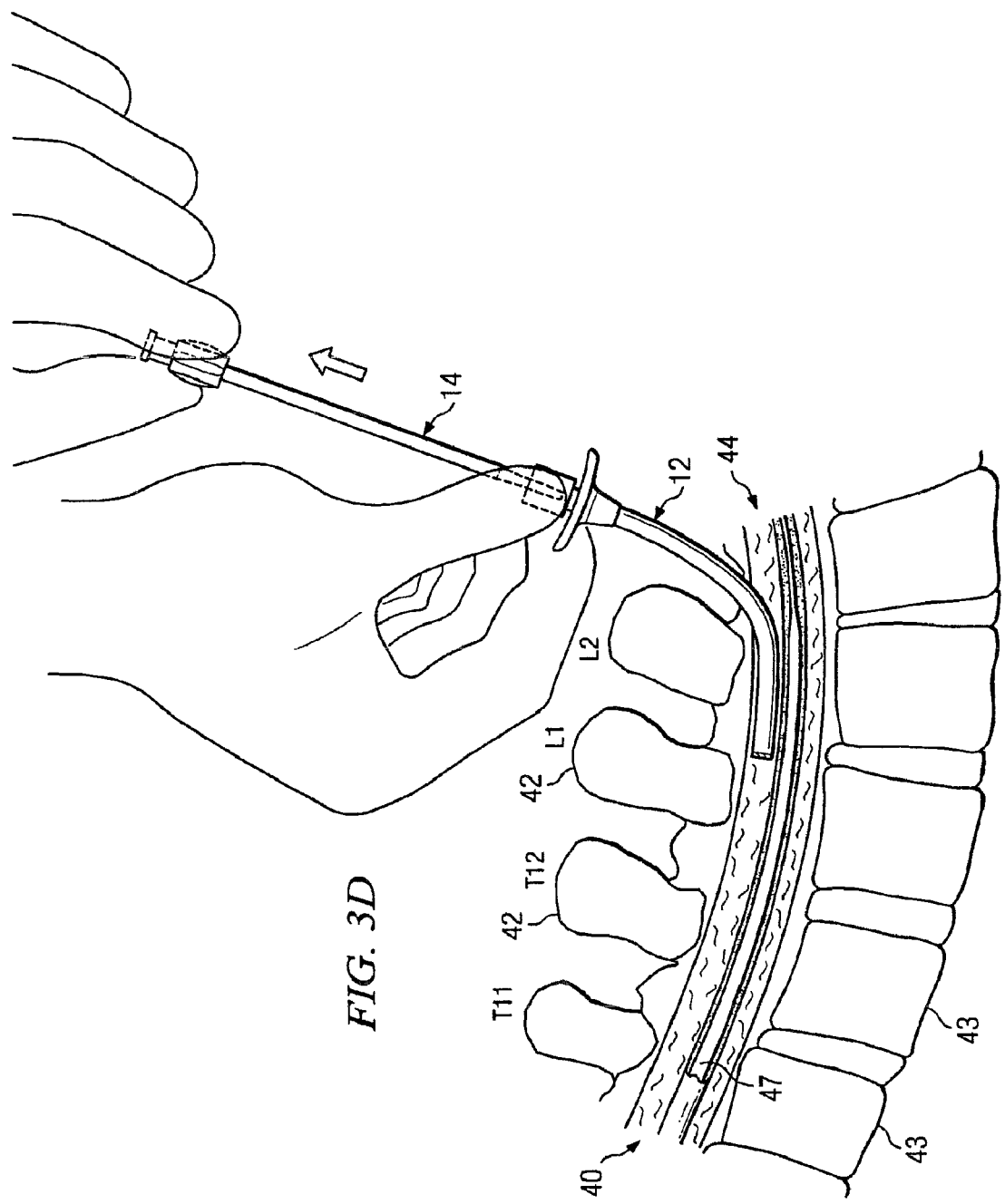
FIG. 3D illustrates an example of an inner penetrator being removed from the outer sheath of an introducer in a human's epidural space.
Figure 3E:
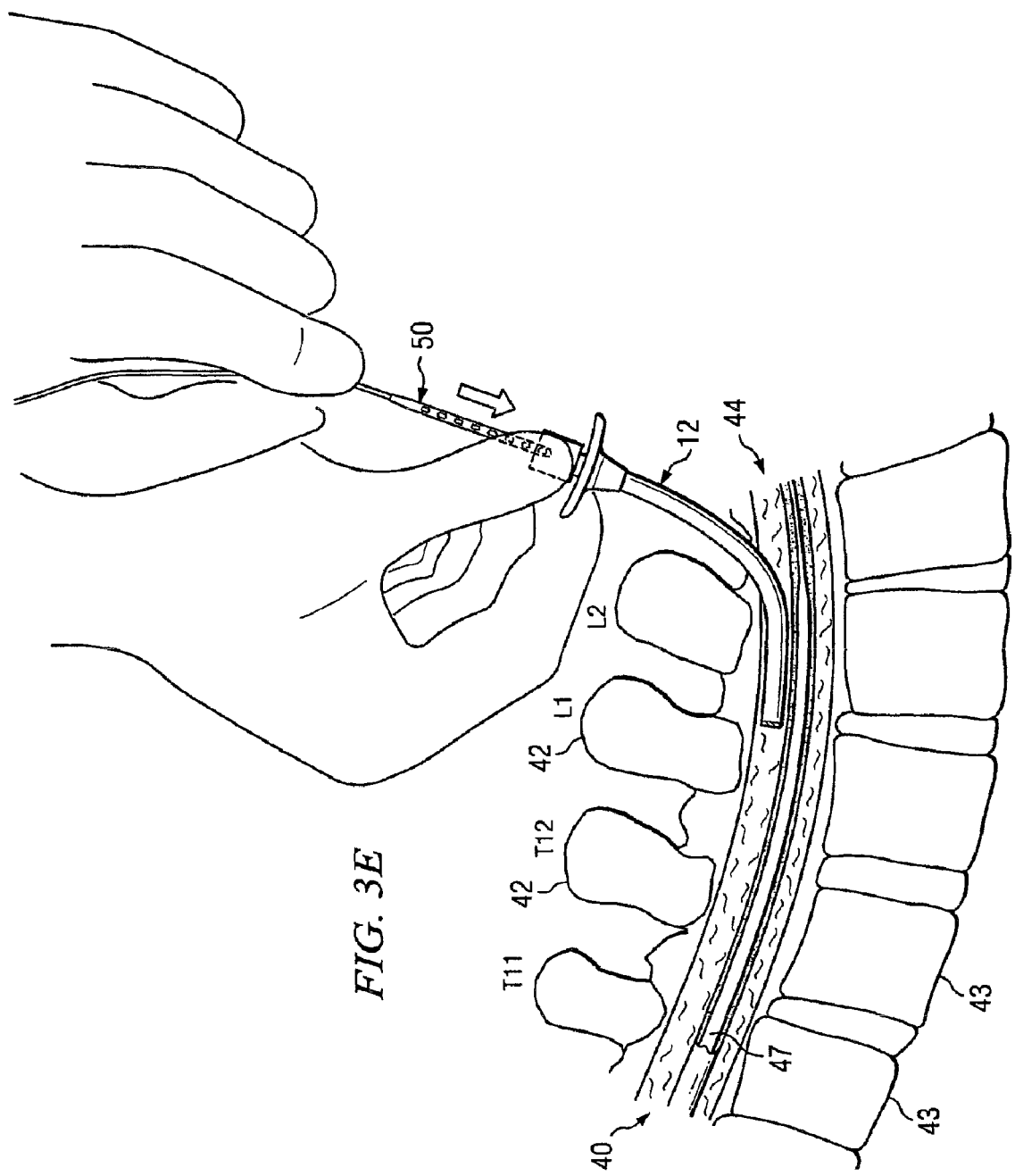
FIG. 3E illustrates an example of a paddle style lead being inserted through an introducer into a human's epidural space.
Figure 3F:
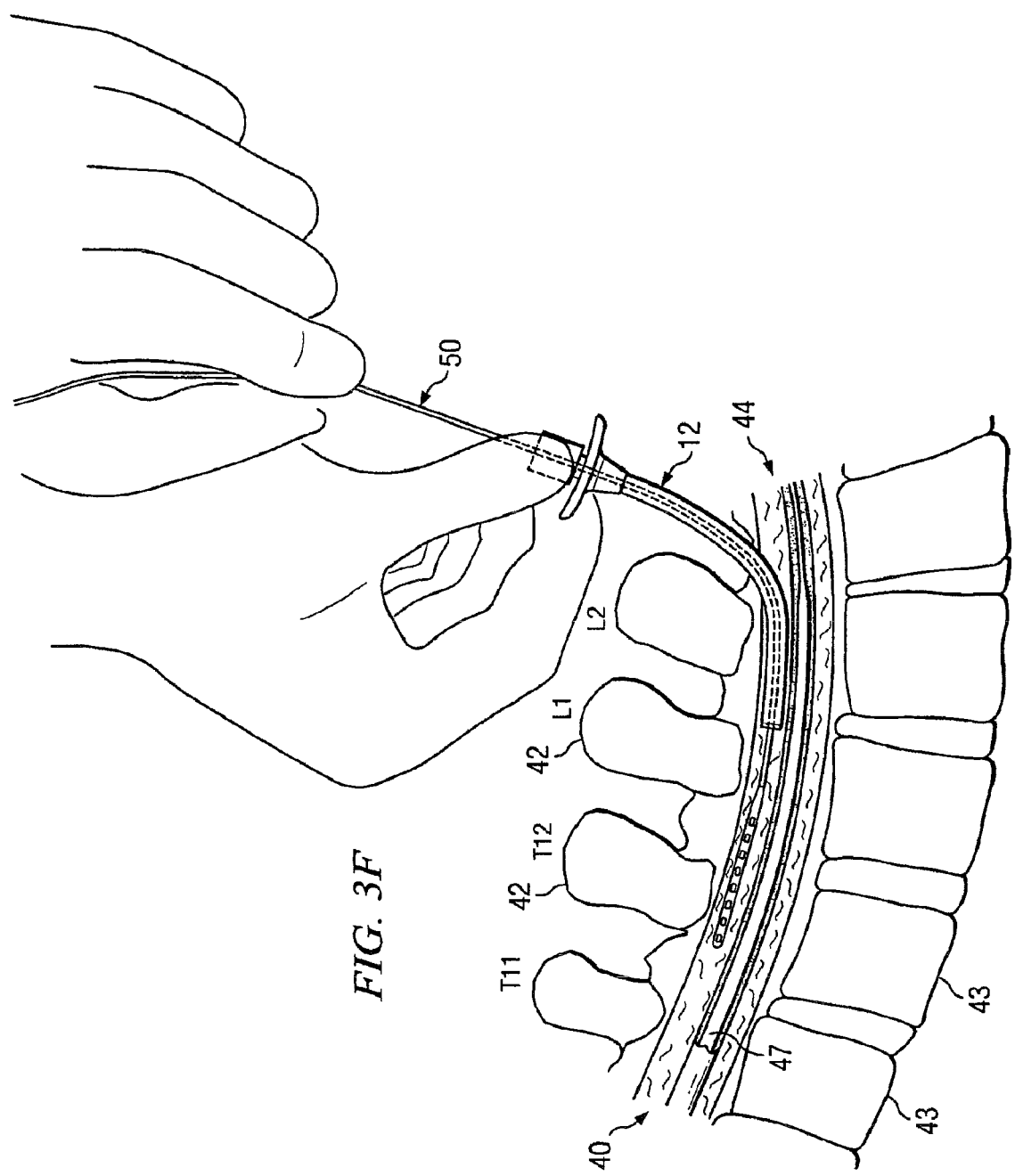
FIG. 3F illustrates an example of a paddle style lead implanted in a human's epidural space.

Once introducer 10 has completely penetrated ligamentum flavum, inner penetrator 14 and guide wire 46 may be removed, leaving outer sheath 12 positioned in epidural space 40, as shown in FIG. 3D. As shown in FIG. 3E, paddle style lead 50 may then be inserted through outer sheath 12 and positioned at an optimal vertebral level, using fluoroscopy for example, for the desired therapeutic effect. As shown in FIG. 3F, outer sheath 12 may then be removed leaving only paddle style lead 50 in epidural space 40, where paddle style lead 50 can be further manipulated if necessary to achieve a desired therapeutic effect. Paddle style lead 50 may be secured by suturing it to a spinous process. In some embodiments, a removable stylet may be inserted into a channel extending within and along the length of lead 50 and manipulated by the operator in order to help steer lead 50 into position, such as described in U.S. Publication No. 2002/0022873, filed on Aug. 10, 2001, for example. The stylet may also provide additional rigidity to lead 50, which may be desired in particular applications.

As described above, introducer 10 may be used to implant paddle style lead 50 into epidural space 40 for spinal nerve stimulation. The same or an analogous, perhaps smaller, introducer 10 may be used to implant an analogous paddle style lead 50 into any appropriate region of the body for peripheral nerve stimulation. For example, such a paddle style lead 50 may have an outer sheath 12 and lumen 28 with a width of approximately 1 mm to approximately 3 mm.

A similar method of insertion (not expressly shown) may be used to implant a paddle style electrical stimulation lead into a human's peripheral nerve tissue. In this embodiment of the invention a site for insertion in tissue near a nerve is selected. The first step in performing the procedure is to insert a needle into the skin and through the subcutaneous tissue and into tissue near a peripheral nerve. If the needle has a stylet, it may be removed and a guide wire may be inserted through the needle and into the tissue near a peripheral nerve. A guide wire may not be required. Fluoroscopy may or may not be used to guide insertion of a guide wire into tissue near a peripheral nerve. Once the tip of the guide wire, or needle, is in the tissue near a peripheral nerve, introducer 10 may be inserted, preferably at an angle that would depend on the anatomy of the body near the peripheral nerve to be stimulated. As introducer 10 is passed through tissues, it elongates the tract made by a needle or guide wire and spreads the tissue. After positioning introducer 10 in tissue adjacent to the peripheral nerve to be stimulated, inner penetrator 14 is removed. A paddle style lead may then be inserted through outer sheath 12. Outer sheath 12 may then be removed leaving only the paddle style lead in position near the peripheral nerve to be stimulated.

Now referring to FIGS. 4A and 4B, there are shown two embodiments of a stimulation system 200, 300 in accordance with the present invention. The stimulation systems generate and apply a stimulus to a tissue or to a certain location of a body. In general terms, the system 200, 300 includes a stimulation or energy source 210, 310 and a lead 50 for application of the stimulus. The lead 110 shown in FIGS. 4A and 4B is the paddle style lead 50 of the present invention.

As shown in FIG. 4A, the stimulation system 200 includes the lead 50 that is coupled to the stimulation source 210. In one embodiment, the stimulation source 210 includes an implantable pulse generator (IPG). As is known in the art, an implantable pulse generator (IPG) is implanted within the body (not shown) that is to receive electrical stimulation from the stimulation source 210. An example IPG may be one manufactured by Advanced Neuromodulation Systems, Inc., such as the Genesis® System, part numbers 3604, 3608, 3609, and 3644, or the Eon® System, part numbers 65-3716, 65-3851, and 64-1254.

As shown in FIG. 4B, the stimulation system 300 includes the lead 50 that is coupled to the stimulation source 310. The stimulation source 310 includes a wireless receiver. As is known in the art, the stimulation source 310 comprising a wireless receiver is implanted within the body (not shown) that is to receive electrical stimulation from the stimulation source 310. An example wireless receiver 310 may be those wireless receivers manufactured by Advanced Neuromodulation Systems, Inc., such as the Renew® System, part numbers 3408 and 3416.

The wireless receiver (not shown) within stimulation source 310 is capable of receiving wireless signals from a wireless transmitter 320. The wireless signals are represented in FIG. 4B by wireless link symbol 330. The wireless transmitter 320 and a controller 340 are located outside of the body that is to receive electrical stimulation from the stimulation source 310. A user of the stimulation source 310 may use the controller 340 to provide control signals for the operation of the stimulation source 310. The controller 340 provides control signals to the wireless transmitter 320. The wireless transmitter 320 transmits the control signals (and power) to the receiver in the stimulation source 310 and the stimulation source 310 uses the control signals to vary the signal parameters of the electrical signals that are transmitted through lead 110 to the stimulation site. An example wireless transmitter 320 may be those transmitters manufactured by Advanced Neuromodulation Systems, Inc., such as the Renew® System, part numbers 3508 and 3516.

As will be appreciated, the connectors are not visible in FIGS. 4A and 4B because the contact electrodes are situated within a receptacle (not shown) of the stimulation source 210, 310. The connectors are in electrical contact with a generator (not shown) of electrical signals within the stimulation source 210, 310. The stimulation source 210, 310 generates and sends electrical signals via the lead 50 to the electrodes 160. Understandably, the electrodes 160 are located at a stimulation site (not shown) within the body that is to receive electrical stimulation from the electrical signals. A stimulation site may be, for example, adjacent to one or more nerves in the central nervous system (e.g., spinal cord) or peripheral nerves. The stimulation source 210, 310 is capable of controlling the electrical signals by varying signal parameters (e.g., intensity, duration, frequency) in response to control signals that are provided to the stimulation source 210, 310.

As described above, once lead 110 is inserted into either the epidural space or near the peripheral nerve, introducer 10 is removed. Lead 110 extends from the insertion site to the implant site (the area of placement of the generator). The implant site is typically a subcutaneous pocket that receives and houses the IPG or receiver (providing stimulation source 210, 310). The implant site is usually positioned a distance away from the stimulation site, such as near the buttocks or other place in the torso area. In most cases, the implant site (and insertion site) is located in the lower back area, and lead 110 may extend through the epidural space (or other space) in the spine to the stimulation site (e.g., middle or upper back, neck, or brain areas). Once the system is implanted, the system of leads and/or extensions may be subject to mechanical forces and movement in response to body movement. FIG. 5 illustrates the steps that may be used to implant a stimulation system 200, 300 into a human.

FIGS. 6A-6E illustrate an example method of removing an implanted paddle style electrical stimulation lead 50 from a human's epidural space 40 using introducer 10*b* according to one embodiment of the invention. Such method may be used to remove an electrical stimulation lead 50 for any suitable reason, such as to relocate, replace, or repair the lead 50, for example. As discussed below, the method may be particularly advantageous for removing a lead 50 around which tissue may have grown and is thus firmly secured within the body. Although the method is discussed with reference to introducer 10*b*, the method may be similarly performed using any suitable introducer, such as introducer 10*a*, for example.

Figure 6A:
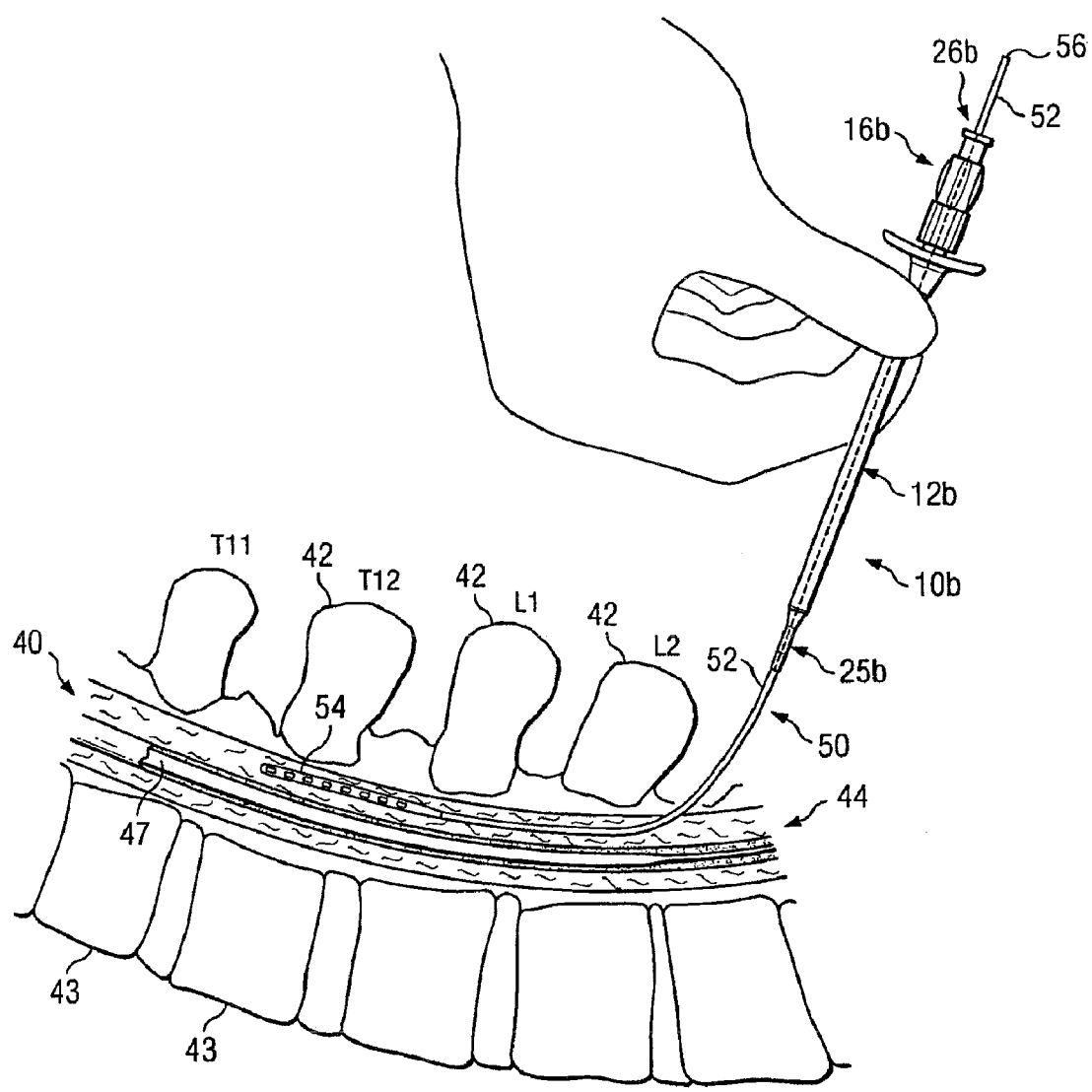
FIGS. 6A-6E illustrate an example method of removing an implanted paddle style electrical stimulation lead from a human's epidural space using an introducer according to one embodiment of the invention.

As shown in FIG. 6A, a paddle style electrical stimulation lead 50 having a body portion 52 and a stimulating portion 54 may be implanted in a human's epidural space 40 in order to stimulate a nerve, such as discussed above regarding the method shown in FIGS. 3A-3F, for example. An end 56 of lead 50 extends out of the epidural space 40 and, in some cases, out through the person's skin or into a subcutaneous pocket formed during implantation Introducer 10*b*, including inner penetrator 14*b* inserted into outer sheath 12*b*, may be inserted around body portion 52 of lead 50 such that end 56 of lead 50 runs though inner channel 22*b* of inner penetrator 14*b*. As shown in FIG. 6A, introducer 10*b* may be advanced such that end 56 of lead 50 protrudes through opening 26*b* in handle portion 16*b* of inner penetrator 14*b*.

Figure 6B:
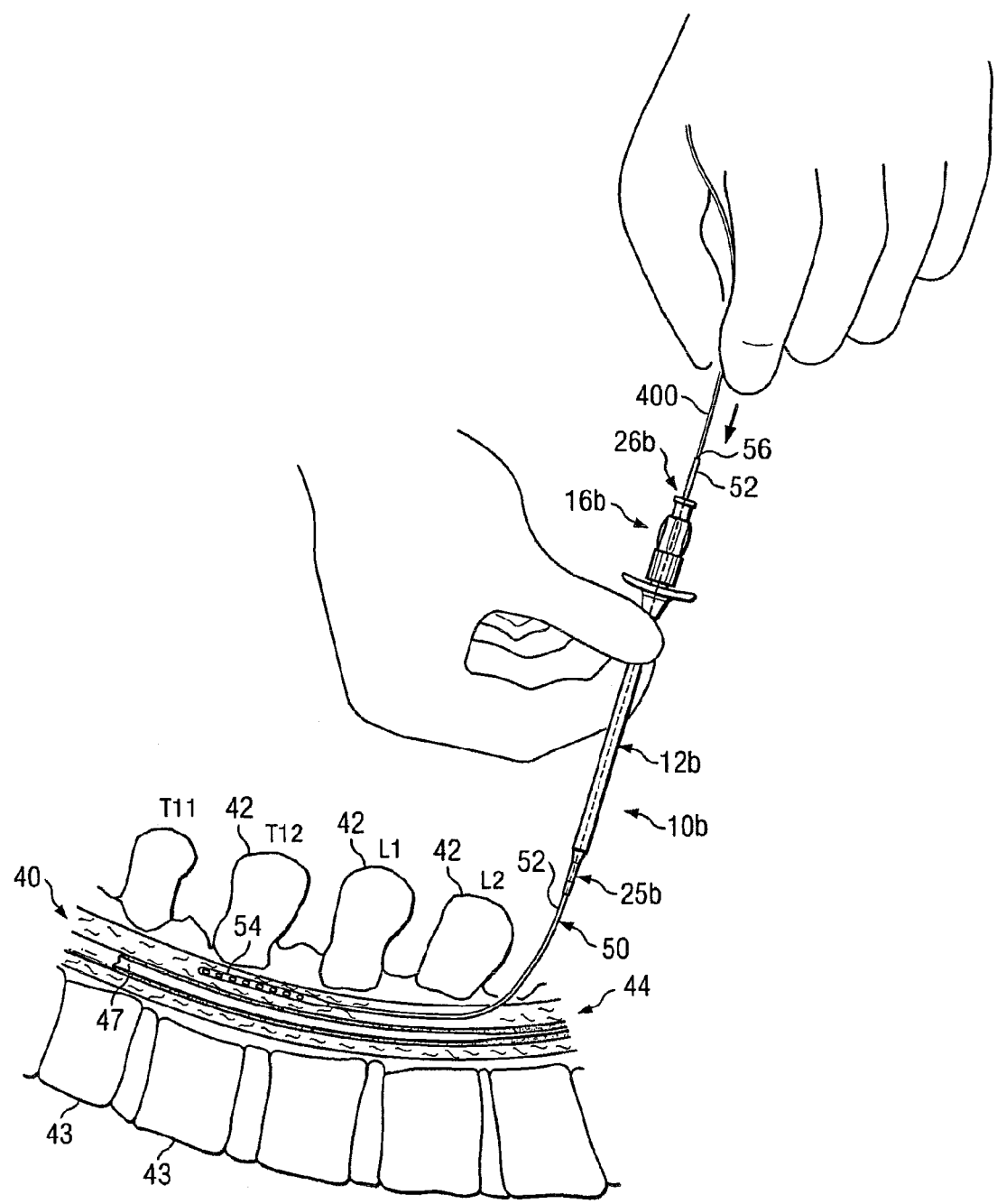

As shown in FIG. 6B, in some embodiments or situations, a stylet 400 may be inserted into a channel that extends along the length of lead 50, if appropriate. For example, stylet 400 may be a stylet typically used for guiding lead 50 during the positioning of lead 50 within the body. Stylet 400 may be advanced partially or completely along the length of lead 50, and may be advanced into stimulating portion 54 of lead 50. As discussed below, stylet 400 is inserted into lead 50 in order to increase the rigidity of lead 50 such that when the introducer 10*b* advances along flexures in body portion 52 of lead 50, tip region 25*b* of inner penetrator 14*b* and/or other portions of introducer 10*b* may flex to substantially follow the flexures in body portion 52 of lead 50.

Figure 6C:
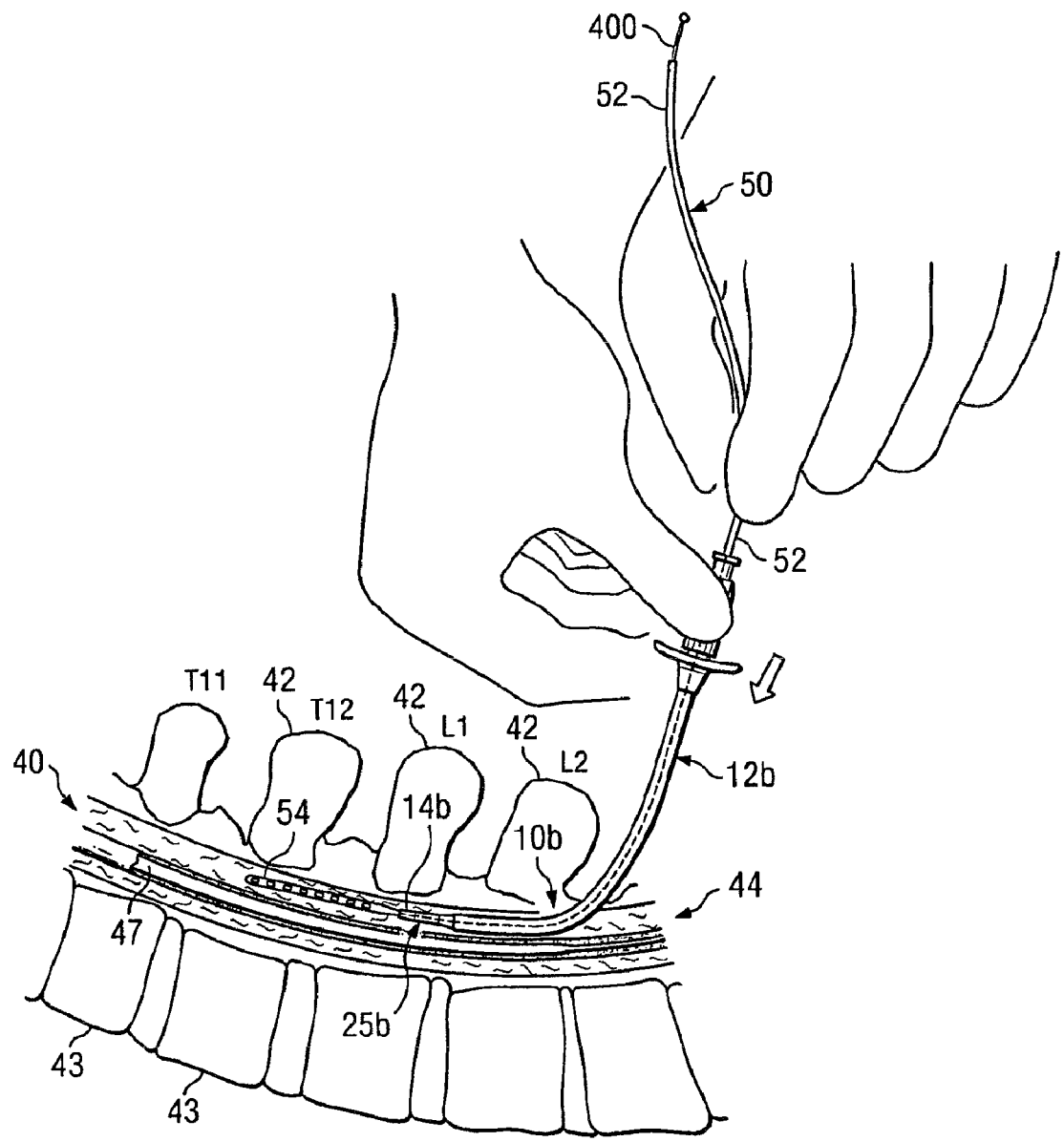

As shown in FIG. 6C, introducer 10*b* may be advanced along body portion 52 of lead 50 until tip region 25*b* of inner penetrator 14*b* is adjacent with, or comes into contact with, stimulating portion 54 of lead 50. As it advances, introducer 10*b* may separate tissue from body portion 52 of lead 50, such as tissue that may have formed around body portion 52 over time, thus creating a passageway through the body. In situations in which body portion 52 extends out through the skin, the operator may choose to cut the skin around the entry point of lead 50 with a scalpel to facilitate subsequent entry of introducer 10. In addition, as introducer 10*b* advances along flexures in body portion 52 of lead 50, due at least in part to the added strength added to lead 50 by stylet 400, tip region 25*b* of inner penetrator 14*b* and/or all or portions of outer sheath 12*b* may flex to maneuver around obstructions or physical structures in the body (such as a spinous process 42, vertebrae 43, or any other structure in the body) and/or to substantially follow curvatures in body portion 52 of lead 50, rather than displacing portions of lead 50, which may cause damage to the body or lead 50. An example of such flexing is shown and discussed below with reference to FIGS. 7A-7D. In some embodiments, this part of the procedure may be performed under fluoroscopic guidance. For example, fluoroscopy may identify radio-opaque markers 34b and 35b on inner penetrator 14b and outer sheath 12b, as well as radio-opaque portions of lead 50, such that the operator (e.g., doctor) may determine the relative positions of introducer 10b and lead 50 during the procedure.

Figure 6D:
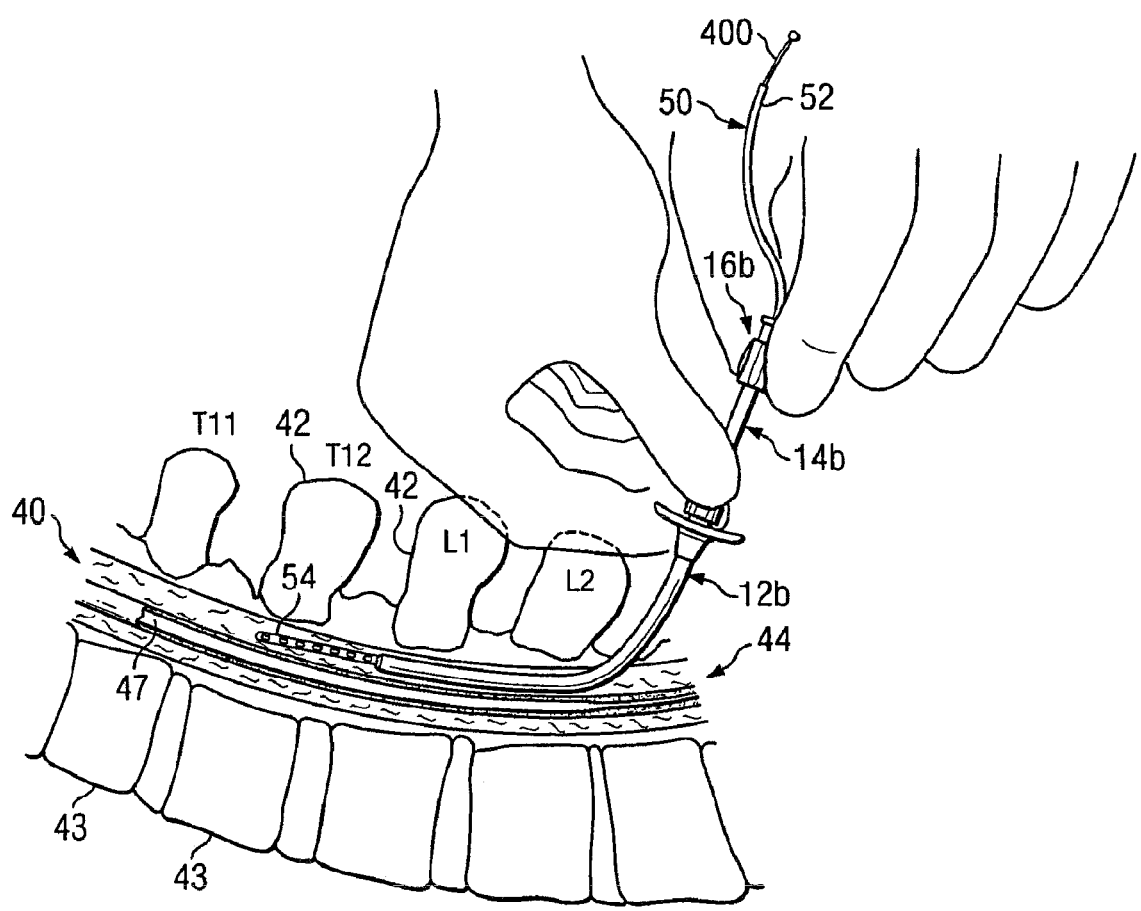

As shown in FIG. 6D, when introducer 10b has been advanced until inner penetrator 14b is adjacent with or contacting stimulating portion 54 of lead 50, outer sheath 12b may be advanced forward (e.g. by sliding) relative to inner penetrator 14b until outer sheath 12b covers at least a portion of stimulation portion 54 of lead 50. Outer sheath 12b may be advanced forward until it completely covers stimulation portion 54 of lead 50. Advancing outer sheath 12b over stimulation portion 54 may separate tissue from stimulating portion 54, such as tissue that may have grown attached to stimulating portion 54. In some embodiments, this part of the procedure may be performed under fluoroscopic guidance. For example, fluoroscopy may identify radio-opaque markers 34b and 35b on inner penetrator 14b and outer sheath 12b, as well as radio-opaque portions of lead 50, such that the operator (e.g., doctor) may determine the relative positions of inner penetrator 14b, outer sheath 12b, and stimulating portion 54 of lead 50 during the procedure.

Figure 6E:
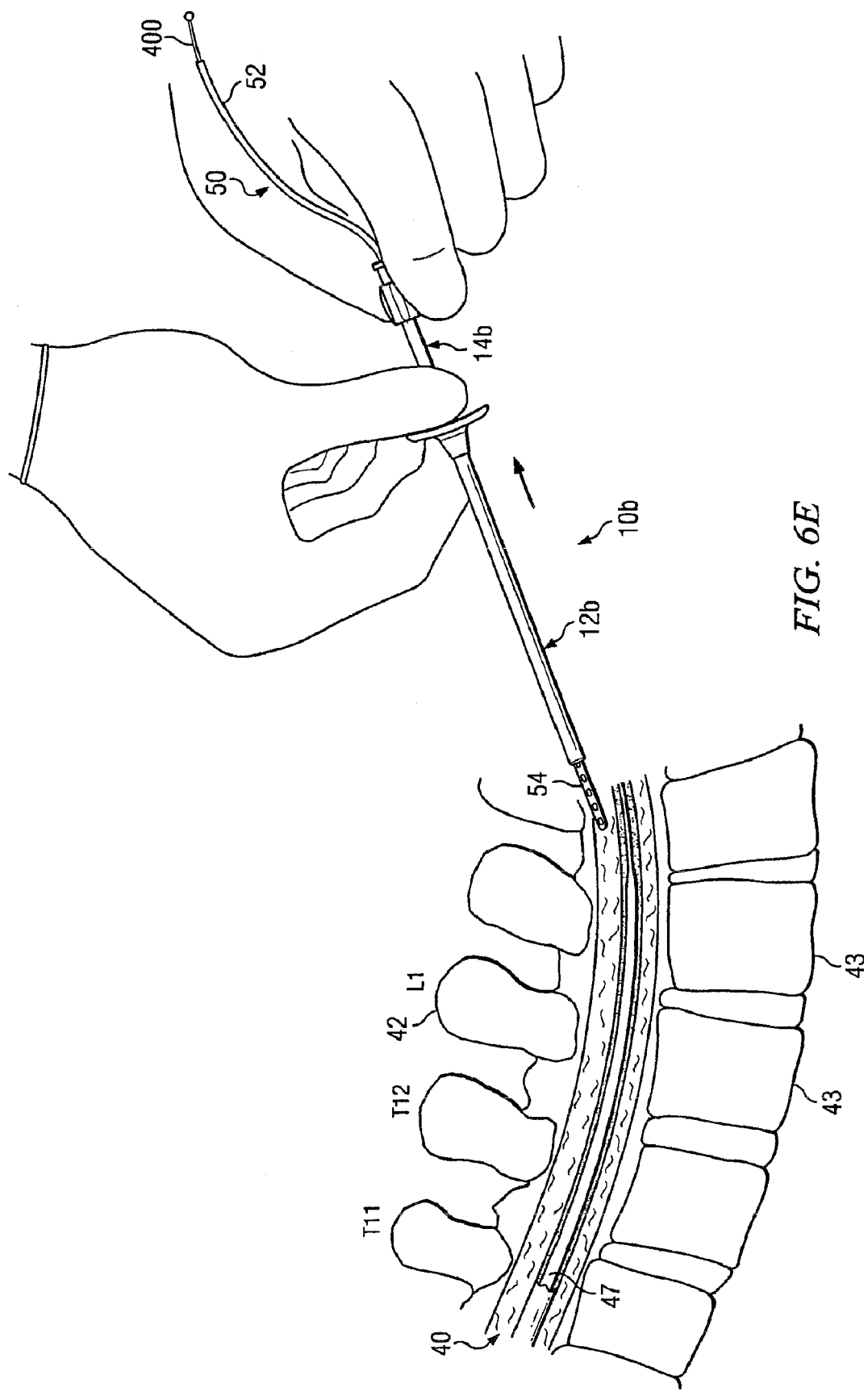

As shown in FIG. 6E, inner penetrator 14b, outer sheath 12b, and lead 50 may all be removed together through the passageway created by advancing introducer 10b along lead 50, as discussed above regarding FIG. 6C. In this manner, lead 50 may be removed from the body without causing significant damage to the body or to the lead 50. As discussed above, the method may be particularly advantageous for removing a lead 50 around which tissue may have grown and is thus firmly secured within the body.

FIGS. 7A-7D illustrate example views of introducer 10b flexing as it moves along a guide wire 46 or stimulation lead 50 within the body, in accordance with certain embodiments of the invention. In particular, all or portions of tip portion 25b of inner penetrator 14b may substantially flex to follow bands or curves in guide wire 46 or stimulation lead 50. In some embodiments, due to the relative shapes and dimensions (e.g., the relative wall thicknesses) of tip transition region 36b, middle transition region 37b, and body transition region 38b, tip transition region 36b may be the most flexible, followed by middle transition region 37b, followed by body transition region 38b. In addition, in some embodiments, such as where outer sheath 12b is formed from a polymer, all or portions of outer sheath 12b may also flex to partially or substantially follow curvatures in guide wire 46 or stimulation lead 50, such as shown in FIGS. 7C and 7D, for example.

Such flexibility of inner penetrator 14b and/or outer sheath 12b may provide several advantages, as discussed above. First, such flexibility may be advantageous for navigating introducer 10b into particular regions in the body, such as the epidural region, for example, which may also reduce the likelihood of introducer 10b damaging tissue in the body. Also, such flexibility may partially or substantially prevent introducer 10b from displacing guide wire 46 as introducer 10b moves along guide wire 46 (which displacement may disrupt the lead insertion or removal process and/or damage tissue in the body.

Figure 8:
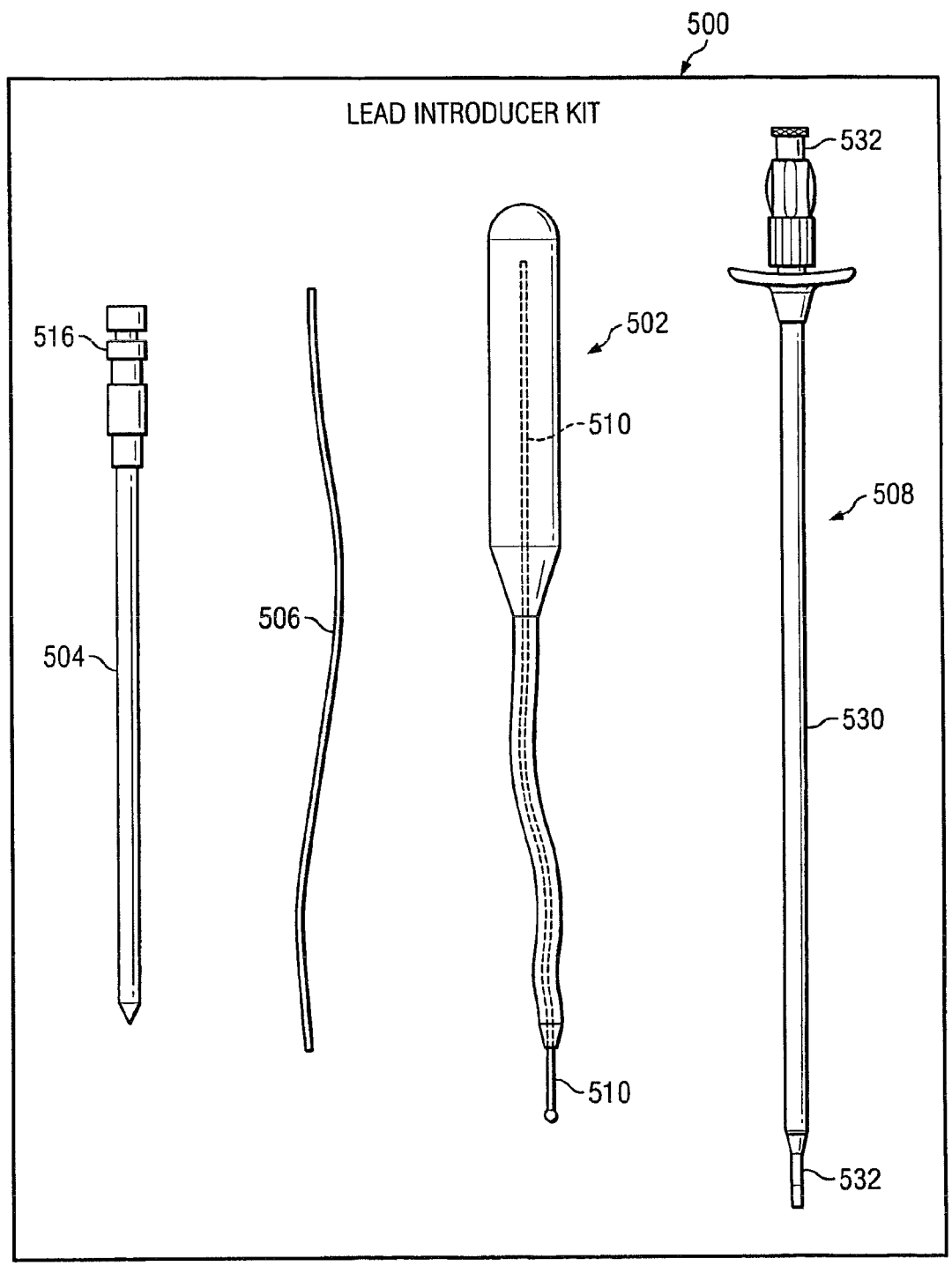
FIG. 8 illustrates an example lead introducer kit for preparing to implant an electrical stimulation lead for electrical stimulation of nerve tissue in a human, according to one embodiment of the invention.

FIG. 8 illustrates an example lead introducer kit 500 for preparing to implant an electrical stimulation lead for electrical stimulation of nerve tissue in a human, according to one embodiment of the invention. Generally, lead introducer kit 500 includes a lead blank 502 and one or more various tools or accessories for preparing for implanting an actual electrical stimulation lead into a human body. The lead blank 502 may be used, for example, to determine whether an actual electrical stimulation lead to be implanted will fit into the target location in the body. For example, an electrical stimulation lead may not fit into the epidural space due to scar tissue or other blockages within the epidural space. Thus, if it is determined using lead blank 502 that an electrical stimulation lead will not fit into the target location in the body, the electrical stimulation lead need not be removed from its packaging, thus allowing the electrical stimulation lead to be used on another patient or at a later time. This may be advantageous due to the relatively high cost of some electrical stimulation leads.

In the embodiment shown in FIG. 8, lead introducer kit 500 includes lead blank 502, a needle 504, and a guide wire 506, and a lead introducer 508. Lead introducer kit 500 may include other tools or accessories for preparing to implant an electrical stimulation lead, but in preferred embodiments does not include the actual electrical stimulation lead. Lead blank 502 may have an identical or similar shape and size as an electrical stimulation lead to be inserted into the body for electrical stimulation of nerve tissue. As discussed above, lead blank 502 may be configured for insertion into the human body to determine whether the electrical stimulation lead may be inserted into the desired location proximate the nerve tissue to be stimulated. For example, lead blank 502 may be configured for insertion into the human body using the various methods and/or devices discussed herein, or using any other known methods and/or devices.

Figure 9:
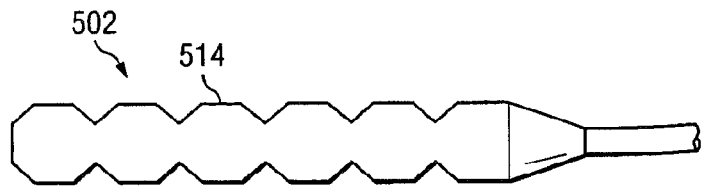
FIG. 9 illustrates an example lead blank including a paddle style stimulating portion having a scalloped shape.

Lead blank 502 may include a removable stylet 510 which may be used for steering lead blank 502 during insertion and/or positioning of lead blank 502. Stylet 510 may be inserted into a channel extending within lead blank 502 and manipulated by an operator in order to help steer lead blank 502. In addition, in some embodiments, the shape of lead blank 502 may be configured to facilitate steering of lead blank 502. For example, lead blank 502 may be a paddle shape with one or more indentions, notches, or score lines that may increase the flexibility of lead blank 502. For instance, FIG. 9 illustrates an example lead blank 502 including a paddle style portion 514 having a scalloped shape. The scalloped shape may increase the flexibility and steerability of lead blank 502.

Needle 504 may include any needle suitable for inserting guide wire 506 into a desired location in the body, such as a human's epidural space, for example, such as needle 41 discussed above regarding the method of FIGS. 3A-3F. Needle 504 may include a removable stylet 516, such as stylet 45 discussed above, for example.

Lead introducer 508 may include any one or more devices for inserting lead blank 502 into the human body. In some embodiments, lead introducer 508 may comprise introducer 10 or introducer 10b described herein, or any other suitable lead introducer. Thus, in some embodiments, lead introducer 508 may include an outer sheath 530 and an inner penetrator 532. Outer sheath 530 may be inserted into a human body near nerve tissue to be stimulated. Inner penetrator 532 may be removably housed within outer sheath 530 and may include an inner channel configured to receive and be advanced along guide wire 506 to a desired location relative to the nerve tissue to be stimulated. Inner penetrator 532 may then be removed from outer sheath 530, leaving outer sheath 530 substantially in position for insertion (or attempted insertion) of lead blank 502 through the outer sheath to determine whether an actual electrical stimulation lead may be properly inserted into position proximate the nerve tissue to be stimulated. Thus, as discussed above, if lead blank 502 will not fit into the target location in the body, it may be determined that the actual electrical stimulation lead will similarly not fit into the target location. Thus, the electrical stimulation lead, which may be included in a separate kit or otherwise packaged separately from lead introducer kit 500, need not be removed from its packaging, thus avoiding wasting an electrical stimulation lead, which may be relatively expensive.

Figure 10:
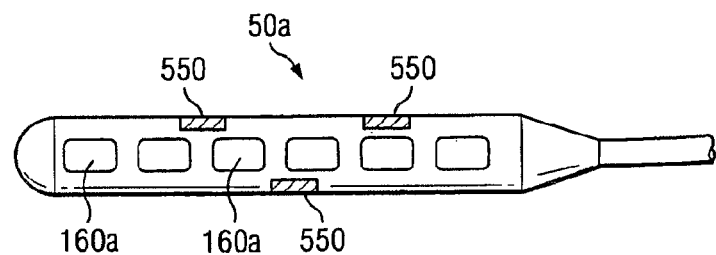
FIG. 10 illustrates an example paddle style electrical stimulation lead having electrodes on only one side, and markings indicating the directional orientation of the lead, according to one embodiment of the invention.

FIG. 10 illustrates an example paddle style electrical stimulation lead 50a having electrodes on only one side, and markings indicating the directional orientation of the lead 50a, according to one embodiment of the invention. Paddle style lead 50a may include any suitable number of electrodes 160a. Electrodes 160a may be flat electrodes that emit energy out of only of the two sides. Such electrodes 160a may be desirable for very small paddle leads, for example. Since the electrodes 160a emit energy out of only one side, the orientation (i.e., which side is facing in which direction) of the paddle style lead 50a may be important, particularly when implanting the lead 50a adjacent the target nerve tissue.

Thus, lead 50a may include one or more markers 550 that may be detected by one or more medical imaging techniques (such as ultrasound, fluoroscopy, MRI, fMRI and/or X-ray, for example) to indicate the directional orientation of the lead 50a. For example, lead 50a may include one or more radio-opaque markers 550 having particular shapes or relative locations such that the operator may determine the orientation of the lead 50a.

Figure 11:
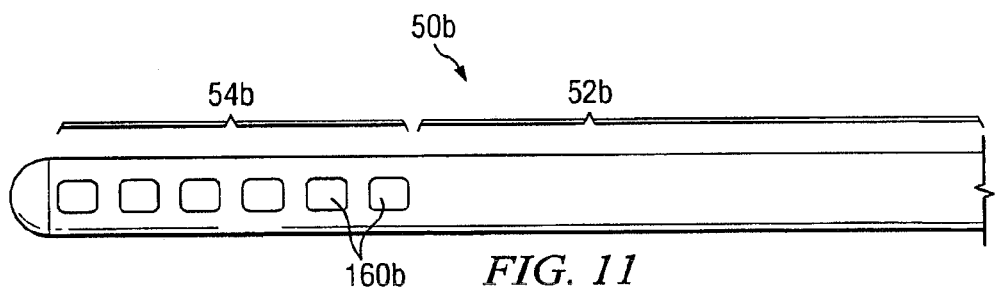
FIG. 11 illustrates an example paddle style electrical stimulation lead having a substantially uniform paddle-shaped cross-section extending along the body of the lead, according to one embodiment of the invention.

FIG. 11 illustrates an example paddle style electrical stimulation lead 50b having a substantially uniform paddle-shaped cross-section extending along the body of the lead 50b, according to one embodiment of the invention. Paddle style lead 50b includes a body portion 52b and a stimulating portion 54b, and a number of electrodes 160b located at stimulating portion 54b. The cross-section of paddle style stimulating portion 54b, which may be, for example, a substantially oval, oblong, or rectangular cross-section, may substantially extend along all or at least a significant portion of the length of body portion 52b. In some embodiments, the substantially uniform cross-section may extend at least to a point outside the epidural region, or outside the skin. In particular embodiments, the substantially uniform cross-section may extend all the way back to the stimulation or power source. This uniform cross-section may make it easier to remove lead 50b from a human body as compared with leads having a smaller cross-sectioned lead body. For example, epidural tissue may grow around an implanted lead body over time. Such tissue may impede the removal of traditional paddle style leads. The substantially uniform cross-section of paddle style lead 50b prevents or reduces the ability of such tissue to impede the removal of implanted lead 50b from the body.

Figure 12:
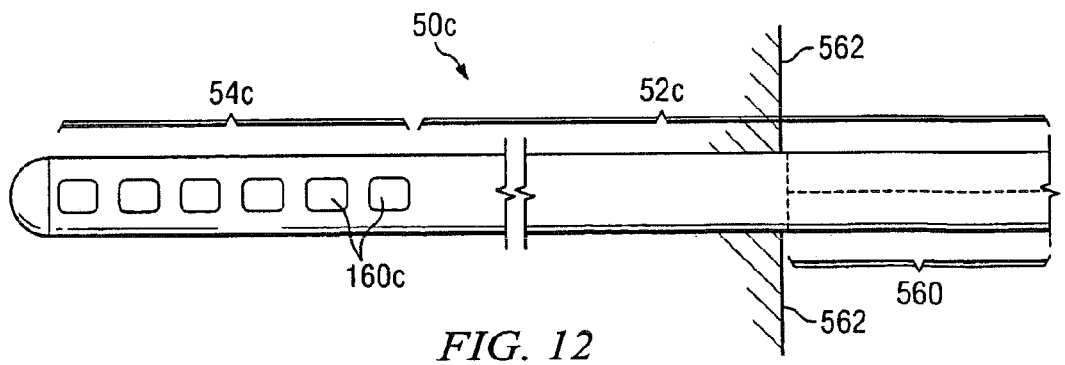
FIG. 12 illustrates an example paddle style electrical stimulation lead having a tear away body portion, according to one embodiment of the invention.

FIG. 12 illustrates an example paddle style electrical stimulation lead 50c having a tear away body portion, according to one embodiment of the invention. Paddle style lead 50c may be similar to paddle style lead 50b shown in FIG. 11. In particular, paddle style lead 50c may includes a body portion 52c, a stimulating portion 54c, a number of electrodes 160c located at stimulating portion 54c, and a substantially uniform cross-section (such as a substantially oval, oblong, or rectangular cross-section, for example) extending back along body portion 52c. Body portion 52c may include a tear-away portion 560 that may be torn away or otherwise removed, revealing a small cross-sectioned lead body (such as a standard lead body wire or cord, for example) that may extend back to the stimulation or power source. Tear-away portion 560 is indicated by perforated tear lines 562. However, tear-away portion 560 may have any other configuration and may be removed in any other suitable manner. In some embodiments, such as shown in FIG. 12, the distance from stimulating portion 54c to tear-away portion 560 may be selected or designed such that when lead 50c is implanted in the body, the forward edge of tear-away portion 560 may be located near or just outside the epidural region 562, or the skin. Thus, lead 50c may provide the advantage of being relatively easy to remove from the body (due to the substantially uniform cross-section, as discussed above), as well as providing a smaller, more manageable body portion 54c leading back to the stimulation or power source.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed:

1. An introducer for implanting an electrical stimulation lead to enable electrical stimulation of nerve tissue, comprising:
    an outer sheath to accommodate insertion of the electrical stimulation lead through the outer sheath, the outer sheath operable to be inserted into a human body near the nerve tissue, the outer sheath including at least one ridge positioned at a first end of the outer sheath, the at least one ridge being at least partially circumferentially positioned about the first end of the outer sheath, the at least one ridge for providing an indication to a user that the outer sheath has contacted a part of the anatomy; and
    an inner penetrator removably housed within the outer sheath and comprising (i) an inner channel configured to accommodate a guide wire, (ii) a tip end having a cross-sectional shape and size substantially conforming to a cross-sectional shape and size of the guide wire, (iii) a body region having a cross-sectional shape and size substantially conforming to a cross-sectional shape and size of the outer sheath, and (iv) one or more transition regions substantially connecting the tip end with the body region;
    wherein the inner penetrator is configured to be advanced along the guide wire to a desired location relative to the nerve tissue and removed from the outer sheath leaving the outer sheath substantially in position for insertion of the electrical stimulation lead through the outer sheath into position proximate the nerve tissue;
    wherein the one or more transition regions include a tip transition region extending from the tip end of the inner penetrator at least a portion of the distance toward the body region of the inner penetrator, and during the advancement of the introducer along the guide wire, the tip transition region flexes to substantially follow flexures in the guide wire, the tip transition region being formed from a particular material and having a wall thickness that decreases toward the tip end of the inner penetrator.

2. The introducer of claim 1, wherein the cross-sectional shape and size of the tip end of the inner penetrator are significantly different than the cross-sectional shape and size of the body region of the inner penetrator.

3. The introducer of claim 1, wherein the outer sheath and the body region of the inner penetrator have substantially oval or oblong cross-sections, and the guide wire and the tip end of the inner penetrator have substantially circular cross-sections.

4. The introducer of claim 1, wherein the outer sheath and inner penetrator are configured from one or more flexible materials such that the introducer may flex to navigate around physical structures in the body.

5. The introducer of claim 1, wherein both the outer sheath and the inner penetrator are formed from one or more of plastic, silastic, or a polymeric materials.

6. The introducer of claim 1, wherein the one or more transition regions include a tip transition region extending from the tip end of the inner penetrator at least a portion of the distance toward the body region of the inner penetrator, the tip transition region being formed from a particular material and having a wall thickness sufficiently thin such that when the inner penetrator is advanced along the guide wire, the tip transition region may flex to substantially follow flexures in the guide wire.

7. The introducer of claim 6, wherein the wall thickness of tip transition region decreases toward the tip end of the inner penetrator.

8. An introducer for implanting an electrical stimulation lead into the epidural space of a patient to enable electrical stimulation of nerve tissue, comprising:

an outer sheath to accommodate insertion of the electrical stimulation lead through the outer sheath, the outer sheath adapted for insertion into the epidural space of the patient, the outer sheath including at least one ridge positioned at a first end of the outer sheath, the at least one ridge being at least partially circumferentially positioned about the first end of the outer sheath, the at least one ridge for providing an indication to a user that the outer sheath has contacted a part of the anatomy; and an inner penetrator removably housed within the outer sheath and comprising (i) an inner channel configured to accommodate a guide wire, (ii) a tip end having a cross-sectional shape and size substantially conforming to a cross-sectional shape and size of the guide wire, (iii) a body region having a cross-sectional shape and size substantially conforming to a cross-sectional shape and size of the outer sheath, and (iv) a plurality of flexing transition regions substantially connecting the tip end with the body region;

wherein at least a portion of the plurality of transition regions are adapted to flex to substantially follow flexures in the guide wire during advancement of the introducer along the guide wire;

wherein the outer sheath, the inner penetrator, and the plurality of transition regions allow the introducer, during entry within the epidural space, to assume a shape where a distal first portion of the introducer possesses a substantially linear shape within the epidural space and a second portion of the introducer exhibits a curve to allow the introducer to exit from the patient's body.

9. The introducer of claim 8, wherein the introducer flexes to navigate around physical structures in the body during advancement of the introducer along the guide wire.

10. The introducer of claim 8, wherein:

the guide wire and the tip end of the inner penetrator have substantially circular cross-sections; and the outer sheath and the body region of the inner penetrator have substantially oval cross-sections.

11. The introducer of claim 8, wherein:

the plurality of transition regions include a tip transition region extending from the tip end of the inner penetrator at least a portion of the distance toward the body region of the inner penetrator; and during the advancement of the introducer along the guide wire, the tip transition region flexes to substantially follow flexures in the guide wire, the tip transition region being formed from a particular material and having a wall thickness that decreases toward the tip end of the inner penetrator.

12. The introducer of claim 8, wherein the plurality of transition regions include a tip transition region extending from the tip end of the inner penetrator at least a portion of the distance toward the body region of the inner penetrator, the tip transition region having a substantially circular cross-section extending along the length of the tip transition region, the substantially circular cross-section having an inner diameter and an outer diameter, both the inner diameter and the outer diameter of the substantially circular cross-section tapering toward the tip end of the tip transition region.

13. The introducer of claim 8, wherein the plurality of transition regions include a tip transition region, a body transition region, and a middle transition connecting the tip transition region with the body transition region, the tip transition region and the body transition region being tapered, and the middle transition not being tapered.

14. An introducer for implanting an electrical stimulation lead to enable electrical stimulation of nerve tissue, comprising:

an outer sheath to accommodate insertion of the electrical stimulation lead through the outer sheath, the outer sheath adapted for insertion into a human body near nerve tissue, the outer sheath including at least one ridge positioned at a first end of the outer sheath, the at least one ridge being at least partially circumferentially positioned about the first end of the outer sheath, the at least one ridge for providing an indication to a user that the outer sheath has contacted a part of the anatomy; and an inner penetrator removably housed within the outer sheath and comprising (i) an inner channel configured to accommodate a guide wire, (ii) a tip end having a cross-sectional shape and size substantially conforming to a cross-sectional shape and size of the guide wire, (iii) a body region having a cross-sectional shape and size substantially conforming to a cross-sectional shape and size of the outer sheath, and (iv) a plurality of flexing transition regions substantially connecting the tip end with the body region;

wherein the tip end of the inner penetrator comprises (i) a needle nose segment that possesses an approximately constant outer diameter, the needle nose segment comprising an aperture for providing an interference fit with the guide wire and (ii) a transition segment that transitions from the shape of the needle nose segment to the shape of the body portion of the inner penetrator.

15. The introducer claim 14 wherein the needle nose segment is more flexible than the transition segment and the transition segment is more flexible than the body portion of the inner penetrator.

* * * * *